United States Patent
Phillips et al.

(10) Patent No.: US 10,588,576 B2
(45) Date of Patent: Mar. 17, 2020

(54) METHODS AND DEVICE FOR DETERMINING A VALID INTRINSIC FREQUENCY

(71) Applicant: NeoSync, Inc., Newport Beach, CA (US)

(72) Inventors: James William Phillips, Fountain Valley, CA (US); Yi Jin, Irvine, CA (US)

(73) Assignee: NeoSync, Inc., Newport Beach, CA (US)

( * ) Notice: Subject to any disclaimer, the term of this patent is extended or adjusted under 35 U.S.C. 154(b) by 926 days.

(21) Appl. No.: 14/827,107

(22) Filed: Aug. 14, 2015

(65) Prior Publication Data
US 2016/0045756 A1    Feb. 18, 2016

Related U.S. Application Data

(60) Provisional application No. 62/038,148, filed on Aug. 15, 2014.

(51) Int. Cl.
*A61N 2/00* (2006.01)
*A61B 5/00* (2006.01)

(52) U.S. Cl.
CPC .......... *A61B 5/7225* (2013.01); *A61B 5/7257* (2013.01)

(58) Field of Classification Search
CPC ........ A61N 2/02; A61N 2/006; A61B 5/4094; A61B 5/0482; A61B 5/0476; A61B 5/048
See application file for complete search history.

(56) References Cited

U.S. PATENT DOCUMENTS

| 3,821,949 A | 7/1974 | Hartzell et al. |
| 4,727,857 A | 3/1988 | Hoerl |

(Continued)

FOREIGN PATENT DOCUMENTS

| DE | 3417773 | 2/1985 |
| DE | 29821635 U1 | 7/1999 |

(Continued)

OTHER PUBLICATIONS

Angelakis et al., EEG Neurofeedback: A brief overview and an example of peak alpha frequency training for cognitive enhancement in the elderly, Clin. Neuropsychol., 21(1):110-29 (2007).

(Continued)

*Primary Examiner* — Etsub D Berhanu
*Assistant Examiner* — Michael A Catina
(74) *Attorney, Agent, or Firm* — Wilson Sonsini Goodrich & Rosati

(57) ABSTRACT

Described are methods and a device for determining a valid intrinsic alpha frequency. Described herein are methods and a device for determining the appropriate intrinsic alpha frequency (IAF) to be applied for neuro-EEG synchronization therapy using alternating magnetic fields to gently "tune" the brain and affect the mood, focus and cognition of subjects. Methods and a device described herein use an algorithm to quantitatively analyze EEG recordings to determine if recorded EEG frequencies are valid, and if necessary, requiring additional recordings and analysis until a valid EEG is found. Methods and devices described herein can be utilized to calculate the intrinsic frequency of other EEG bands, including the Theta, Beta Gamma and Delta bands.

20 Claims, 5 Drawing Sheets

EEG Discrimination Algorithm Flowchart

(56) References Cited

U.S. PATENT DOCUMENTS

| | | |
|---|---|---|
| 5,036,858 A | 8/1991 | Carter et al. |
| 5,092,835 A | 3/1992 | Schurig et al. |
| 5,409,445 A | 4/1995 | Rubins |
| 5,453,072 A | 9/1995 | Anninos et al. |
| 5,496,258 A | 3/1996 | Anninos et al. |
| 5,632,720 A | 5/1997 | Kleitz |
| 5,667,469 A | 9/1997 | Zhang et al. |
| 5,691,324 A | 11/1997 | Sandyk |
| 5,697,883 A | 12/1997 | Anninos et al. |
| 5,707,334 A | 1/1998 | Young |
| 5,769,778 A | 6/1998 | Abrams et al. |
| 5,788,624 A | 8/1998 | Lu et al. |
| 5,817,000 A | 10/1998 | Souder |
| 5,935,054 A | 8/1999 | Loos |
| 5,954,629 A | 9/1999 | Yanagidaira et al. |
| 6,001,055 A | 12/1999 | Souder |
| 6,083,252 A | 7/2000 | King et al. |
| 6,157,278 A | 12/2000 | Katznelson et al. |
| 6,194,852 B1 | 2/2001 | Lovatt et al. |
| 6,231,497 B1 | 5/2001 | Souder |
| 6,234,953 B1 | 5/2001 | Thomas et al. |
| 6,238,333 B1 | 5/2001 | Loos |
| 6,266,556 B1 | 7/2001 | Ives et al. |
| 6,290,638 B1 | 9/2001 | Canedo et al. |
| 6,402,678 B1 | 6/2002 | Fischell et al. |
| 6,463,328 B1 | 10/2002 | John |
| 6,488,617 B1 | 12/2002 | Katz |
| 6,537,197 B1 | 3/2003 | Ruohonen et al. |
| 6,648,812 B2 | 11/2003 | Ardizzone |
| 6,663,557 B2 | 12/2003 | Werny |
| 6,679,825 B2 | 1/2004 | Alicea |
| 6,978,179 B1 | 12/2005 | Flagg et al. |
| 7,033,312 B2 | 4/2006 | Rohan et al. |
| 7,102,144 B2 | 9/2006 | Matsuda et al. |
| 7,258,659 B2 | 8/2007 | Anninou et al. |
| 7,282,021 B2 | 10/2007 | Rohan et al. |
| 7,297,100 B2 | 11/2007 | Thomas et al. |
| 8,465,408 B2 | 6/2013 | Phillips et al. |
| 8,475,354 B2 | 7/2013 | Phillips et al. |
| 8,480,554 B2 | 7/2013 | Phillips et al. |
| 8,585,568 B2 | 11/2013 | Phillips et al. |
| 8,870,737 B2 | 10/2014 | Phillips et al. |
| 8,888,672 B2 | 11/2014 | Phillips et al. |
| 8,888,673 B2 | 11/2014 | Phillips et al. |
| 8,926,490 B2 | 1/2015 | Phillips et al. |
| 8,961,386 B2 | 2/2015 | Phillips et al. |
| 9,015,057 B2 | 4/2015 | Phillips et al. |
| 9,272,159 B2 | 3/2016 | Phillips et al. |
| 9,308,387 B2 | 4/2016 | Phillips et al. |
| 9,446,259 B2 | 9/2016 | Phillips et al. |
| 9,456,784 B2 | 10/2016 | Helekar et al. |
| 9,649,502 B2 | 5/2017 | Phillips et al. |
| 9,962,555 B1 | 5/2018 | Charles |
| 10,065,048 B2 | 9/2018 | Phillips |
| 2002/0007128 A1 | 1/2002 | Ives et al. |
| 2002/0147380 A1 | 10/2002 | Ardizzone |
| 2002/0153015 A1 | 10/2002 | Garibaldi et al. |
| 2002/0183587 A1 | 12/2002 | Dormer |
| 2003/0093028 A1 | 5/2003 | Spiegel |
| 2004/0138578 A1 | 7/2004 | Pineda et al. |
| 2004/0143296 A1 | 7/2004 | Wang et al. |
| 2004/0210102 A1 | 10/2004 | Van Mullekom |
| 2005/0043774 A1 | 2/2005 | Devlin et al. |
| 2005/0070778 A1 | 3/2005 | Lackey et al. |
| 2005/0107654 A1 | 5/2005 | Riehl et al. |
| 2005/0107655 A1 | 5/2005 | Holzner |
| 2005/0118266 A1 | 6/2005 | Khan et al. |
| 2005/0118286 A1 | 6/2005 | Suffin et al. |
| 2005/0124847 A1 | 6/2005 | Ardizzone et al. |
| 2005/0124848 A1 | 6/2005 | Holzner |
| 2005/0154426 A1 | 7/2005 | Boveja et al. |
| 2005/0182287 A1 | 8/2005 | Becker |
| 2005/0187423 A1 | 8/2005 | Ardizzone et al. |
| 2005/0228209 A1 | 10/2005 | Schneider et al. |
| 2005/0256539 A1 | 11/2005 | George et al. |
| 2006/0015153 A1 | 1/2006 | Gliner et al. |
| 2006/0058572 A1 | 3/2006 | Anninou et al. |
| 2006/0094924 A1 | 5/2006 | Riehl et al. |
| 2006/0149119 A1 | 7/2006 | Wang |
| 2006/0161039 A1 | 7/2006 | Juliana et al. |
| 2006/0189866 A1 | 8/2006 | Thomas et al. |
| 2006/0212090 A1 | 9/2006 | Lozano et al. |
| 2006/0217781 A1 | 9/2006 | John et al. |
| 2006/0258950 A1 | 11/2006 | Hargrove et al. |
| 2006/0287566 A1 | 12/2006 | Zangen et al. |
| 2007/0004957 A1 | 1/2007 | Hilburg |
| 2007/0100389 A1 | 5/2007 | Jaax et al. |
| 2007/0106170 A1 | 5/2007 | Dunseath, Jr. et al. |
| 2007/0142874 A1 | 6/2007 | John et al. |
| 2007/0179558 A1 | 8/2007 | Gliner et al. |
| 2007/0191727 A1 | 8/2007 | Fadem |
| 2007/0203390 A1 | 8/2007 | Rohan et al. |
| 2007/0208209 A1 | 9/2007 | Holcomb |
| 2007/0282156 A1 | 12/2007 | Konings |
| 2008/0009772 A1 | 1/2008 | Tyler et al. |
| 2008/0046013 A1 | 2/2008 | Lozano |
| 2008/0081941 A1 | 4/2008 | Tononi |
| 2008/0125669 A1 | 5/2008 | Suffin et al. |
| 2008/0262287 A1 | 10/2008 | Dussau |
| 2009/0082690 A1 | 3/2009 | Phillips et al. |
| 2009/0198144 A1 | 8/2009 | Phillips et al. |
| 2009/0204015 A1 | 8/2009 | Phillips et al. |
| 2010/0185042 A1 | 7/2010 | Schneider et al. |
| 2011/0034822 A1 | 2/2011 | Phillips et al. |
| 2011/0112427 A1* | 5/2011 | Phillips .............. A61B 5/048 |
| | | 600/544 |
| 2011/0118536 A1 | 5/2011 | Phillips et al. |
| 2011/0137104 A1 | 6/2011 | Phillips et al. |
| 2013/0144107 A1 | 6/2013 | Phillips et al. |
| 2013/0144108 A1 | 6/2013 | Phillips et al. |
| 2013/0150650 A1 | 6/2013 | Phillips et al. |
| 2014/0121446 A1 | 5/2014 | Phillips et al. |
| 2014/0163305 A1 | 6/2014 | Watterson |
| 2014/0179980 A1 | 6/2014 | Phillips et al. |
| 2014/0276182 A1 | 9/2014 | Helekar et al. |
| 2017/0120066 A1 | 5/2017 | Phillips et al. |
| 2017/0312536 A1 | 11/2017 | Phillips et al. |
| 2018/0126184 A1 | 5/2018 | Phillips |
| 2018/0214710 A1 | 8/2018 | Charles |
| 2018/0229049 A1 | 8/2018 | Phillips |

FOREIGN PATENT DOCUMENTS

| | | |
|---|---|---|
| EP | 2197534 A1 | 6/2010 |
| EP | 2498857 A1 | 9/2012 |
| JP | 2008543416 A | 12/2008 |
| WO | WO-9615829 A2 | 5/1996 |
| WO | WO-9629114 A1 | 9/1996 |
| WO | WO-03058518 A2 | 7/2003 |
| WO | WO-2006134598 A2 | 12/2006 |
| WO | WO-2007067148 A1 | 6/2007 |
| WO | WO-2008074707 A1 | 6/2008 |
| WO | WO-2009036040 A1 | 3/2009 |
| WO | WO-2009042718 A1 | 4/2009 |
| WO | WO-2009042720 A1 | 4/2009 |
| WO | WO-2009042721 A1 | 4/2009 |
| WO | WO-2009042722 A1 | 4/2009 |
| WO | WO-2011017466 A1 | 2/2011 |
| WO | WO-2011059986 A1 | 5/2011 |
| WO | WO-2018136431 A1 | 7/2018 |

OTHER PUBLICATIONS

Anninos et al., "MEG evaluation of Parkinson's diseased patients after external magnetic stimulation," Acta neurol. Belg. 107:5-10 (2007).

Anninos et al., "Nonlinear Analysis of Brain Activity in Magnetic Influenced Parkinson Patients," Brain Topography 13(2):135-144 (2000).

Applied Signal Processing. (2004) 20 pgs., http://users.abo.fi/htoivone/courses/sbappl/asp_chapter1.pdf.

(56) References Cited

OTHER PUBLICATIONS

Arns et al., "Potential differential effects of 9Hz rTMS and 10 Hz rTMS in the treatment of depression," Letter to the Editor, Brain Stimulation (2010), 3, 124-126.
Blum, Computer-based electroencephalography: technical basics, basis for new applications, and potential pitfalls, Electroencephalography and Clinical Neurophysiology 106, pp. 118-126 (1998).
Discovery Science: Transcranial Magnetic Stimulation Treatment for Addiction, Autism, Depression (Dr. Yi Jin) from PopSci's Future of Pleasure originally broadcast Oct. 26, 2009 [online][retrieved on Dec. 16, 2011] Retrieved from the Internet: http://www.youtube.com/watch?v=E3tPuB31CYc.
EP08833077 Supplementary Search Report and Written Opinion dated Dec. 21, 2010.
First Annual Brain and Behavior Symposium: The Future of the Brain (Dr. Yi Jin) (Jun. 8, 2007) [online][retrieved on Dec. 16, 2011] Retrieved from the Internet: http://neurosciencecenter.brooksideinstitute.com/2007_symposium_03Speaker.asp.
Gasquet et al., "Pharmacological treatment and other predictors of treatment outcomes in previously untreated patients with schizophrenia; results from the European Schizophrenia Outpatient Health Outcomes (SOHO) study," Int. Clin. Psychopharmacol. 20:199-205 (2005).
Gaussian Peak Fit VI., LabView 2009 Help. National Instruments. 4 pgs., Jun. 2009.
Hamidi et al., "Repetitive transcranial magnetic stimulation affects behavior by biasing endogenous cortical oscillations," Frontiers in Integrative Neuroscience 3(14):1-12 (2009).
Jin, Y. et al., "Alpha EEG predicts visual reaction time," Int. J. Neurosci. 116:1035-1044 (2006).
Jin, Y. et al., "Therapeutic effects of individualized alpha frequency transcranial magnetic stimulation (alpha TMS) on the negative symptoms of schizophrenia," Schizophr. Bull. 32(3):556-561 (Jul. 2006;Epub Oct. 27, 2005).
Klimesch et al., "EEG alpha oscillations: The inhibition-timing hypothesis," Brain Research Reviews 53:63-88 (2003).
Klimesch et al., "Enhancing cognitive performance with repetitive transcranial magnetic stimulation at human individual alpha frequency," Eur. J. Neuroscience 17:1129-1133 (2003).
Leuchter, et al.The relationship between brain oscillatory activity and therapeutic effectiveness of transcranial magnetic stimulation in the treatment of major depressive disorder. Frontiers in Human Neuroscience. vol. 7, Article 37, pp. 1-12. Feb. 26, 2013.
MERT: Magno-EEG Resonant Therapy (Aug. 29, 2007)[online][retrieved on Dec. 19, 2011] Retrieved from the Internet: http://web.archive.org/web/20080514214345/http://neurosciencecenter.brooksideinstitute.com/mert.asp; http://web.archive.org/web/20080514161113/http://neurosciencecenter.brooksideinstitute.com/mert_disorders.asp; and http://web.archive.org/web/20080509095813/http://neurosciencecenter.brooksideinstitute.com/mertfaq.asp.
Myung, Tutorial on Maximum Likelihood Estimation, Journal of Mathematical Psychology, 47, pp. 90-100 (2003).
O'Haver, Curve Fitting C: Non-Linear Iterative Curve Fitting, Jun. 6, 2009. http://web.archive.org/web/20090606121639/http://terpconnect.umd.edu/~toh/spectrum/CurveFittingC.html.
PCT/US08/77569 International Preliminary Report on Patentability dated Mar. 30, 2010.
PCT/US08/77569 International Search Report dated Jan. 26, 2009.
PCT/US08/77569 Written Opinion dated Jan. 26, 2009.
PCT/US08/77571 International Preliminary Report on Patentability dated Mar. 30, 2010.
PCT/US08/77571 International Search Report dated Nov. 21, 2008.
PCT/US08/77571 Written Opinion dated Nov. 21, 2008.
PCT/US08/77573 International Preliminary Report on Patentability dated Mar. 30, 2010.
PCT/US08/77573 International Search Report dated Nov. 24, 2008.
PCT/US08/77573 Written Opinion dated Nov. 24, 2008.
PCT/US08/77575 International Preliminary Report on Patentability dated Mar. 30, 2010.
PCT/US08/77575 International Search Report dated Dec. 9, 2008.
PCT/US10/056075 International Preliminary Report on Patentability dated May 24, 2012.
PCT/US10/056075 International Search Report and Written Opinion dated Mar. 14, 2011.
PCT/US10/44465 International Preliminary Report on Patentability dated Feb. 7, 2012.
PCT/US10/44465 International Search Report and Written Opinion dated Sep. 29, 2010.
Real-Time Filtering in BioExplorer. Jan. 25, 2007. http://web.archive.org/web/20070125020332/http://www.brain-trainer.com/Filtering.pdf.
Sauseng et al., "Spontaneous locally restricted EEG alpha activity determines cortical excitability in the motor cortex," Neuropsychologia 47:284-288 (2009).
U.S. Appl. No. 12/944,549 Office Action dated Mar. 25, 2014.
U.S. Appl. No. 12/944,549 Office Action dated Sep. 13, 2013.
U.S. Appl. No. 12/237,295 Office Action dated Dec. 6, 2011.
U.S. Appl. No. 12/237,295 Office Action dated May 23, 2014.
U.S. Appl. No. 12/237,295 Office Action dated May 9, 2011.
U.S. Appl. No. 12/237,295 Office Action dated Oct. 21, 2013.
U.S. Appl. No. 12/237,304 Office Action dated Feb. 12, 2015.
U.S. Appl. No. 12/237,304 Office Action dated Jul. 3, 2012.
U.S. Appl. No. 12/237,304 Office Action dated Sep. 25, 2013.
U.S. Appl. No. 12/237,319 Office Action Jul. 19, 2012.
U.S. Appl. No. 12/237,319 Office Action Oct. 14, 2011.
U.S. Appl. No. 12/237,328 Office Action dated Jul. 19, 2012.
U.S. Appl. No. 12/237,328 Office Action dated Oct. 12, 2011.
U.S. Appl. No. 12/850,547 Office Action dated Jul. 19, 2012.
U.S. Appl. No. 12/850,547 Office Action dated Oct. 13, 2011.
U.S. Appl. No. 12/942,922 Office Action dated Nov. 19, 2012.
U.S. Appl. No. 12/944,591 Office Action dated Apr. 7, 2014.
U.S. Appl. No. 13/681,964 Office Action dated Jan. 22, 2014.
U.S. Appl. No. 13/682,057 Office Action dated Jan. 22, 2014.
U.S. Appl. No. 13/682,098 Office Action dated Feb. 11, 2015.
U.S. Appl. No. 13/682,098 Office Action dated Jan. 24, 2014.
U.S. Appl. No. 13/682,098 Office Action dated Jun. 30, 2014.
U.S. Appl. No. 13/682,147 Office Action dated Apr. 25, 2013.
U.S. Appl. No. 13/682,147 Office Action dated Dec. 20, 2013.
U.S. Appl. No. 13/682,181 Office Action dated Feb. 12, 2014.
U.S. Appl. No. 13/682,181 Office Action dated Jun. 27, 2014.
U.S. Appl. No. 13/893,171 Office Action dated Jan. 2, 2015.
U.S. Appl. No. 13/682,057 Office Action dated Mar. 12, 2015.
U.S. Appl. No. 14/051,378 Office Action dated Jan. 5, 2015.
U.S. Appl. No. 12/237,304 Office Action dated Oct. 8, 2015.
U.S. Appl. No. 13/675,466 Office Action dated Aug. 26, 2015.
U.S. Appl. No. 13/682,098 Office Action dated Aug. 14, 2015.
What is TMS? (Jun. 8, 2011) [online][retrieved on Dec. 19, 2011] Retrieved from the Internet: http://web.archive.org/web/20101014023718/http://braintreatmentcenter.com/tms.html; and http://www.braintreatmentcenter.com/addiction.
Japanese Patent Application No. 2017-8983 Office Action dated Nov. 27, 2017.
PCT/US2018/13903 International Search Report and Written Opinion dated May 15, 2018.
U.S. Appl. No. 12/237,304 Office Action dated Oct. 10, 2017.
U.S. Appl. No. 15/232,692 Office Action dated Dec. 14, 2017.
U.S. Appl. No. 15/583,802 Office Action dated Aug. 28, 2017.
European Patent Application No. 08833077.4 Communication dated May 23, 2016.
European Patent Application No. 10830602.8 Communication dated Jun. 30, 2016.
Triggs et al., Effects of Left Frontal Transcranial Magnetic Stimulation on Depressed Mood, Cognition, and Corticomotor Threshold, Society of Biological Psychiatry, 45:1440-1446 (1999).
U.S. Appl. No. 12/237,304 Office Action dated Jan. 6, 2017.
EP18160327.5 European Search Report dated Dec. 24, 2018.
U.S. Appl. No. 12/237,304 Office Action dated Jul. 8, 2016.
U.S. Appl. No. 15/634,351 Office Action dated Sep. 10, 2018.
Japanese Patent Application No. Tokugan2017-096854 Office Action dated Jun. 3, 2019.

(56) References Cited

OTHER PUBLICATIONS

U.S. Appl. No. 15/486,428 Restriction Requirement dated Apr. 11, 2019.
U.S. Appl. No. 15/935,482 Office Action dated Sep. 23, 2019.

* cited by examiner

EEG Discrimination Algorithm Flowchart

Sample 128 second EEG recording showing 16 epochs

Sample IAF estimate of an Epoch

Phase 1

Phase 2

Phase 3

METHODS AND DEVICE FOR DETERMINING A VALID INTRINSIC FREQUENCY

CROSS-REFERENCE TO RELATED APPLICATIONS

The present application is a non-provisional of, and claims the benefit of, U.S. Provisional Application No. 62/038,148 filed on Aug. 15, 2014, the entire contents of which are incorporated herein by reference.

BACKGROUND OF THE INVENTION

Mental disorders generate serious problems for the affected people, their families, and society. Currently, psychiatrists and neurophysiologists treat these disorders with a variety of medications, many of which have significant negative side effects.

Repetitive Transcranial Magnetic Stimulation (rTMS) uses an electromagnet placed on the scalp that generates a series of magnetic field pulses roughly the strength of an MRI scan. Some studies have shown that rTMS can reduce the negative symptoms of schizophrenia, depression and other mental disorders under certain circumstances. The NEST (Neuro-EEG Synchronization Therapy) is specifically tailored to deliver low amplitude stimulation at the patient's intrinsic alpha frequency (IAF). Therefore it is imperative that a stable, repeatable IAF value be obtained.

SUMMARY OF THE INVENTION

Described herein are methods and devices for utilizing an algorithm by which a valid intrinsic alpha frequency (IAF) is determined by quantitatively analyzing EEG recordings one at a time to determine whether or not they are valid, and requiring additional recordings until a valid IAF is found, or until the algorithm determines that a valid IAF cannot be found.

Provided herein is a method of determining a final intrinsic alpha frequency of a subject comprising: applying an EEG discrimination routine comprising: obtaining a first EEG recording in a time domain; dividing the first EEG recording into a plurality of epochs, each comprising a segment of data, wherein a total number of epochs is N; filtering the segment of data of each epoch using a high-pass filter; converting each epoch into a frequency domain epoch (i); filtering each frequency domain epoch (i) using a smoothing filter; calculating an epoch intrinsic alpha frequency ($m_i$) of each frequency domain epoch (i); calculating a mean (M) intrinsic alpha frequency (IAF) of all intrinsic alpha frequencies ($m_{i-N}$), wherein $$M = \frac{1}{N} \sum_{i=1}^{N} m_i;$$

determining a farthest frequency domain epoch ($m_f$) from the mean M, if $|m_f - M| > 0.5$ Hz, removing the farthest frequency domain epoch ($m_f$), decrementing N, and returning to step g), or if $|m_f - M| \leq 0.5$ Hz, continuing to next step; setting a final intrinsic alpha frequency (fIAF) equal to M; and outputting the final intrinsic alpha frequency (fIAF) to a user or to a device.

In some embodiments, wherein determining a farthest frequency domain epoch ($m_f$) from the mean M comprises calculating an index (I) of the frequency domain epoch that is farthest from the mean (M), wherein $I = Index(max_i |m_i - M|)$.

In some embodiments, the first EEG recording length is 128 seconds. In some embodiments, the first EEG recording is a single-channel recording. In some embodiments, the first EEG recording is a multi-channel recording, wherein an IAF estimate is made for each channel in an epoch and averaged together, or wherein each channel is treated separately, generating an IAF estimate for each channel for the full EEG recording, and wherein valid IAF estimates from each channel, as determined by the step; determining a farthest frequency domain epoch ($m_f$) from the mean M, if $|m_f - M| > 0.5$ Hz, removing the farthest frequency domain epoch ($m_f$), decrementing N, and returning to step g), or if $|m_f - M| \leq 0.5$ Hz, are averaged together to generate a final IAF. In some embodiments, a channel of the first EEG recording initially comprises 16 epochs. In some embodiments, the epoch intrinsic alpha frequency ($m_i$) of each frequency domain epoch (i) is calculated from 7.0 Hz to 14.0 Hz. In some embodiments, the final intrinsic alpha frequency (fIAF) is from 8.0 Hz to 13.0 Hz. In some embodiments, the first EEG recording comprises a sample rate of 128 samples/sec. In some embodiments, the high-pass filter comprises a $4^{th}$ order Butterworth IIR filter with the 3 dB cutoff set to 5.0 Hz. In some embodiments, the epoch intrinsic alpha frequency of each epoch ($m_i$) is determined using a Fast Fourier Transform (FFT). In some embodiments, the Fast Fourier Transform (FFT) uses a resolution of 1024 points, which results in a 0.125 Hz resolution per bin from 0 Hz to 64 Hz. In some embodiments, the Fast Fourier Transform (FFT) is smoothed with an averaging filter that averages the 5 points±2 from the target. In some embodiments, if a standard deviation (SD) of the N epoch IAF values ≥0.75 Hz, a second EEG recording is obtained and the previously described method of determining a final intrinsic alpha frequency of a subject (using a first EEG recording) is repeated using the second EEG recording in place of the first EEG recording. In some embodiments, if a second standard deviation (SD) of the N epoch IAF values ≥0.75 Hz obtained using the second EEG recording, a third EEG recording is obtained and the previously described method of determining a final intrinsic alpha frequency of a subject (using a first EEG recording) is repeated using the third EEG recording in place of the first EEG recording. In some embodiments, if a third standard deviation (SD) of the N epoch IAF values ≥0.75 Hz obtained using the third EEG recording, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF). In still other embodiments, if the final intrinsic alpha frequency (fIAF) is <8.0 Hz or >13.0 Hz, a second EEG recording is obtained and the previously described method of determining a final intrinsic alpha frequency of a subject (using a first EEG recording) is repeated using the second EEG recording in place of the first EEG recording. In still other embodiments, if the final intrinsic alpha frequency (fIAF) calculated using the second EEG recording is <8.0 Hz or >13.0 Hz, a third EEG recording is obtained and the previously described method of determining a final intrinsic alpha frequency of a subject (using a first EEG recording) is repeated using the third EEG recording in place of the first EEG recording. In still other embodiments, if the final intrinsic alpha frequency (fIAF)

calculated using the third EEG recording is <8.0 Hz or >13.0 Hz, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF). Still further, in other embodiments, if the final intrinsic alpha frequency (fIAF) of the EEG is from 8.0 Hz-13.0 Hz and the standard deviation (SD) of the N epoch IAF values is <0.75 Hz, the final intrinsic alpha frequency (fIAF) is determined to be a valid intrinsic alpha frequency (vIAF).

In some embodiments of the method of determining a final intrinsic alpha frequency of a subject; if a standard deviation (SD) of the N epoch IAF values ≥0.75 Hz, or if the final intrinsic alpha frequency (fIAF) is <8.0 Hz or >13.0 Hz, then a second EEG recording is obtained and the previously described method of determining a final intrinsic alpha frequency of a subject (using a first EEG recording) is repeated using the second EEG recording in place of the first EEG recording. In some embodiments, if a standard deviation (SD) of the N epoch IAF values calculated using the second EEG reading ≥0.75 Hz, or if the final intrinsic alpha frequency (fIAF) calculated using the second EEG reading is <8.0 Hz or >13.0 Hz, then a third EEG recording is obtained and the previously described method of determining a final intrinsic alpha frequency of a subject (using a first EEG recording) is repeated using the third EEG recording in place of the first EEG recording. In some embodiments, if a standard deviation (SD) of the N epoch IAF values calculated using the third EEG reading ≥0.75 Hz, or if the final intrinsic alpha frequency (fIAF) calculated using the third EEG reading is <8.0 Hz or >13.0 Hz, then a fourth EEG recording is obtained and the previously described method of determining a final intrinsic alpha frequency of a subject (using a first EEG recording) is repeated using the fourth EEG recording in place of the first EEG recording. In some embodiments, if a standard deviation (SD) of the N epoch IAF values calculated using the fourth EEG reading ≥0.75 Hz, or if the final intrinsic alpha frequency (fIAF) calculated using the fourth EEG reading is <8.0 Hz or >13.0 Hz, then a fifth EEG recording is obtained and the previously described method of determining a final intrinsic alpha frequency of a subject (using a first EEG recording) is repeated using the fifth EEG recording in place of the first EEG recording. In some embodiments, if a standard deviation (SD) of the N epoch IAF values calculated using the fifth EEG reading ≥0.75 Hz, or if the final intrinsic alpha frequency (fIAF) calculated using the fifth EEG reading is <8.0 Hz or >13.0 Hz, then a sixth EEG recording is obtained and the previously described method of determining a final intrinsic alpha frequency of a subject (using a first EEG recording) is repeated using the sixth EEG recording in place of the first EEG recording. In some embodiments, if a standard deviation (SD) of the N epoch IAF values calculated using the sixth EEG reading ≥0.75 Hz, or if the final intrinsic alpha frequency (fIAF) calculated using the sixth EEG reading is <8.0 Hz or >13.0 Hz, then a seventh EEG recording is obtained and the previously described method of determining a final intrinsic alpha frequency of a subject (using a first EEG recording) is repeated using the seventh EEG recording in place of the first EEG recording. In some embodiments, if a standard deviation (SD) of the N epoch IAF values calculated using the seventh EEG reading ≥0.75 Hz, or if the final intrinsic alpha frequency (fIAF) calculated using the seventh EEG reading is <8.0 Hz or >13.0 Hz, then a eighth EEG recording is obtained and the previously described method of determining a final intrinsic alpha frequency of a subject (using a first EEG recording) is repeated using the eighth EEG recording in place of the first EEG recording. In some embodiments, if the final intrinsic alpha frequency (fIAF) calculated using the third EEG recording is <8.0 Hz or >13.0 Hz or if the standard deviation (SD) of the N epoch IAF values calculated using the third EEG reading ≥0.75 Hz, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF). In still other embodiments, if the final intrinsic alpha frequency (fIAF) calculated using the eighth EEG recording is <8.0 Hz or >13.0 Hz or if the standard deviation (SD) of the N epoch IAF values calculated using the eighth EEG reading ≥0.75 Hz, a range of fIAF intrinsic alpha frequencies (fIAFs) of the at least three of the first EEG recording, the second EEG recording, the third EEG recording, the fourth EEG recording, the fifth EEG recording, the sixth EEG recording, the seventh EEG recording, the eighth EEG recording is calculated, wherein if the range is <2.0 Hz, then the mean value of the final intrinsic alpha frequencies (fIAFs) of at least three of the first EEG recording, the second EEG recording, the third EEG recording, the fourth EEG recording, the fifth EEG recording, the sixth EEG recording, the seventh EEG recording, the eighth EEG recording is determined to be the Valid intrinsic alpha frequency (vIAF).

Provided herein is a method of determining a final intrinsic alpha frequency of a subject comprising applying an EEG discrimination routine comprising: obtaining a multi-channel EEG recording in a time domain; dividing the multi-channel EEG recording into a plurality of epochs, each epoch comprising a corresponding data segment from each channel, and averaging the data segments in each epoch together, wherein a total number of epochs is N; filtering the data segments of each epoch using a high-pass filter; converting each epoch into a frequency domain epoch (i); filtering each frequency domain epoch (i) using a smoothing filter; calculating an epoch intrinsic alpha frequency ($m_i$) of each frequency domain epoch (i); calculating a mean (M) intrinsic alpha frequency (IAF) of all intrinsic alpha frequencies ($m_{i-N}$), wherein $$M = \frac{1}{N}\sum_{i=1}^{N} m_i;$$

determining a farthest frequency domain epoch ($m_f$) from the mean M, wherein, i) if $|m_f - M| > 0.5$ Hz, removing the farthest frequency domain epoch ($m_f$), decrementing N, and returning to step g), or, ii) if $|m_f - M| \leq 0.5$ Hz, continuing to next step; setting a final intrinsic alpha frequency (fIAF) equal to M; and outputting the final intrinsic alpha frequency (fIAF) to a user or to a device.

In some embodiments, a channel intrinsic alpha frequency (cIAF) is determined for each channel in the frequency domain epoch (i) of a multi-channel EEG recording, and they are averaged together to generate the epoch intrinsic alpha frequency ($m_i$). In some embodiments, the epoch intrinsic alpha frequency ($m_i$) is generated by averaging channel intrinsic alpha frequencies generated from the channels meeting inclusion criteria and averaged together, wherein the inclusion criteria comprise: i) a greatest alpha power as compared to all other channels of the EEG recording; ii) a lowest variance as compared to all other channels of the EEG recording; or iii) a highest Q-factor as compared to all other channels of the EEG recording.

In some embodiments, an epoch intrinsic alpha frequency ($m_i$) is generated by averaging channel intrinsic alpha frequencies generated from the channels meeting inclusion criteria and averaged together, wherein the inclusion criteria comprise: a greatest alpha power as compared to all other channels of the EEG recording; a lowest variance as compared to all other channels of the EEG recording; or a highest Q-factor as compared to all other channels of the EEG recording.

In some embodiments, a multiple-channel time domain EEG recording may be used, wherein different options exist for determining the intrinsic alpha frequency (IAF). In one embodiment, each channel from the first multi-channel time domain EEG recording is treated separately and generates a channel intrinsic alpha frequency (cIAF) for each channel of the full time domain EEG recording, wherein a number of channel intrinsic alpha frequencies (cIAFs) is equal to the number of channels from the first multi-channel time domain EEG recording. In some embodiments, all channel intrinsic alpha frequencies (cIAFs) from the first multi-channel time domain EEG recording are averaged together to obtain a representative intrinsic alpha frequency (IAF) of the multi-channel time domain EEG recording. In some embodiments the channel intrinsic alpha frequency (cIAF) of a single channel of the first multi-channel time domain EEG recording is within a band between 8.0 Hz-13.0 Hz; has a standard deviation (SD) below 0.75 Hz; has the lowest (SD) of all the channel intrinsic alpha frequencies (cIAFs) of the multi-channel time domain EEG recording; and is selected as a representative intrinsic alpha frequency (IAF) of the multi-channel time domain EEG recording. Still further, all channel intrinsic alpha frequencies (cIAFs) of channels of the first multi-channel time domain EEG recording that are within a band between 8.0 Hz-13.0 Hz; and have a standard deviation (SD) below 0.75 Hz; are averaged together to obtain a representative intrinsic alpha frequency (IAF) of the multi-channel time domain EEG recording.

Provided herein is a method of determining a valid intrinsic frequency (vIF) of an EEG band of a subject comprising: applying an EEG discrimination routine comprising: obtaining a first EEG recording in a time domain; dividing the first EEG recording into a plurality of epochs, wherein a total number of epochs is N; filtering the data using a high-pass filter (to reduce the influence of heartbeat and low frequency noise); converting each epoch into a frequency domain epoch (i); filtering each frequency domain epoch (i) using a smoothing filter; calculating an epoch intrinsic frequency ($m_i$) in an EEG band of each frequency domain epoch (i); calculating a mean (M) intrinsic frequency (IF) in the EEG band of all epoch intrinsic frequencies ($m_{i-N}$), wherein $$M = \frac{1}{N}\sum_{i=1}^{N} m_i;$$

determining the farthest frequency domain epoch ($m_f$) from the mean, wherein if $|m_f-M|>0.5$ Hz, removing the farthest frequency domain epoch ($m_f$) decrementing N, and returning to the step for calculating a mean (M) intrinsic frequency (IF) in the band of all epoch intrinsic frequencies, or if $|m_f-M|\leq 0.5$ Hz, then; continue to the next step for setting a final intrinsic frequency (fIF) equal to M; and outputting the final intrinsic frequency (fIF) in the EEG band equal to M; and outputting the final intrinsic frequency (fIF) in the EEG band to a user or device. In some embodiments, wherein determining a farthest frequency domain epoch ($m_f$) from the mean M comprises determining an index (I) of the frequency domain epoch that is farthest from the mean (M), wherein I=Index($max_i|m_i-M|$). In some embodiments, the EEG band comprises: an Alpha band; a Theta band; a Beta band; a Gamma band; and a Delta band. In some embodiments, the EEG recording length is 128 seconds. In some embodiments, the EEG recording is a single-channel recording. In some embodiments, the EEG recording is a multi-channel recording. In some embodiments the EEG is a multi-channel recording, wherein a channel intrinsic frequency (cIF) estimate may be made for each channel in an epoch and averaged together, or wherein each channel is treated separately, generating a final intrinsic frequency (fIF) estimate for each channel for the full EEG recording, and wherein final intrinsic frequency estimates from each channel, as determined by step h), are averaged together to generate a final intrinsic frequency (fIF). In some embodiments, a channel of the EEG comprises 16 epochs. In some embodiments, the calculated epoch intrinsic frequency ($m_i$) of the EEG comprises a range that is at least: ±0.5 Hz outside the range of the EEG band; ±1.0 Hz outside the range of the EEG band; ±1.5 Hz outside the range of the EEG band; and ±2.0 Hz outside the range of the EEG band. In some embodiments, the EEG recording comprises a sample rate of 128 samples/sec. In some embodiments, the high-pass filter uses a $4^{th}$ order Butterworth IIR filter with the 3 dB cutoff set to 5.0 Hz. In some embodiments, the epoch intrinsic frequency of each epoch ($m_i$) is determined using a Fast Fourier Transform (FFT). In some embodiments, the Fast Fourier Transform (FFT) uses a resolution of 1024 points, which results in a 0.125 Hz resolution per bin from 0 Hz to 64 Hz. In some embodiments, the Fast Fourier Transform (FFT) is smoothed with an averaging filter that averages 5 points±2 from the target. In some embodiments, if the standard deviation (SD) of the N epoch IF value is ≥0.75 Hz, a second EEG recording is obtained and the previously described method of determining a valid intrinsic frequency (vIF) of an EEG band of a subject (using a first EEG recording) is repeated using the second EEG recording in place of the first recording. In some embodiments, if the standard deviation (SD) of the N epoch IF values calculated using the second EEG recording is ≥0.75 Hz, a third EEG recording is obtained and the previously described method of determining a valid intrinsic frequency (vIF) of an EEG band of a subject (using a first EEG recording) is repeated using the third EEG recording in place of the first recording. In some embodiments, if the standard deviation (SD) of the N epoch IF values calculated using the third EEG recording is ≥0.75 Hz, a fourth EEG recording is obtained and the previously described method of determining a valid intrinsic frequency (vIF) of an EEG band of a subject (using a first EEG recording) is repeated using the fourth EEG recording in place of the first recording. In some embodiments, if the standard deviation (SD) of the N epoch IF values calculated using the fourth EEG recording is ≥0.75 Hz, a fifth EEG recording is obtained and the previously described method of determining a valid intrinsic frequency (vIF) of an EEG band of a subject (using a first EEG recording) is repeated using the fifth EEG recording in place of the first recording. In some embodiments, if the standard deviation (SD) of the N epoch IF values calculated using the fifth EEG recording is ≥0.75 Hz, a sixth EEG recording is obtained and the previously described method of determining a valid intrinsic frequency (vIF) of an EEG band of a subject (using a first EEG recording) is repeated using the sixth EEG recording in place of the first recording. In some embodiments, if the standard deviation (SD) of the N epoch IF values calculated using the sixth EEG recording is ≥0.75 Hz, a seventh EEG recording is obtained and the previously described method of determining a valid intrinsic frequency (vIF) of an EEG band of a subject (using a first EEG recording) is repeated using the seventh EEG recording in place of the first recording. In some embodiments, if the standard deviation (SD) of the N epoch IF values calculated using the seventh EEG recording is ≥0.75 Hz, an eighth EEG recording is obtained and the previously described method of determining a valid intrinsic frequency (vIF) of an EEG band of a subject (using a first EEG recording) is repeated using the eighth EEG recording in place of the first recording. In still other embodiments, if the eighth standard deviation (SD) of the N epoch IF values is ≥0.75 Hz obtained using the eighth EEG recording, a range of final intrinsic frequencies (fIFs) of at least three of the first EEG recording, the second EEG recording, the third EEG recording, the fourth EEG recording, the fifth EEG recording, the sixth EEG recording, the seventh EEG recording, and the eighth EEG recording is calculated, wherein if the range is <2.0 Hz, then the mean value of the final intrinsic frequencies (fIFs) of at least three of the first EEG recording, the second EEG recording, the third EEG recording, the fourth EEG recording, the fifth EEG recording, the sixth EEG recording, the seventh EEG recording, and the eighth EEG recording is determined to be the Valid intrinsic frequency (vIF). In some embodiments, if a third standard deviation (SD) of the N epoch IF values ≥0.75 Hz obtained using the third EEG recording, a range of final intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). In some embodiments of the method of determining a valid intrinsic frequency (vIF) of an EEG band of a subject, if the final intrinsic frequency (fIF) of the EEG recording is > a predetermined amount outside the EEG band, a second EEG recording is obtained and the method of determining a valid intrinsic frequency (vIF) of an EEG band of a subject is repeated using the second EEG recording in place of the first EEG recording. In some embodiments, the predetermined amount is: ±0.5 Hz; ±1.0 Hz; ±1.5 Hz; or ±2.0 Hz. In some embodiments, if the final intrinsic frequency (fIF) of the EEG recording obtained using the second EEG recording is > the predetermined amount outside the EEG band, a third EEG recording is obtained and the previously described method of determining a valid intrinsic frequency (vIF) of an EEG band of a subject (using a first EEG recording) is repeated using the third EEG recording in place of the first recording. In some embodiments, if the final intrinsic frequency (fIF) of the EEG recording obtained using the third EEG recording is > the predetermined amount outside the EEG band, a fourth EEG recording is obtained and the previously described method of determining a valid intrinsic frequency (vIF) of an EEG band of a subject (using a first EEG recording) is repeated using the fourth EEG recording in place of the first recording. In some embodiments, if the final intrinsic frequency (fIF) of the EEG recording obtained using the fourth EEG recording is > the predetermined amount outside the EEG band, a fifth EEG recording is obtained and the previously described method of determining a valid intrinsic frequency (vIF) of an EEG band of a subject (using a first EEG recording) is repeated using the fifth EEG recording in place of the first recording. In some embodiments, if the final intrinsic frequency (fIF) of the EEG recording obtained using the fifth EEG recording is > the predetermined amount outside the EEG band, a sixth EEG recording is obtained and the previously described method of determining a valid intrinsic frequency (vIF) of an EEG band of a subject (using a first EEG recording) is repeated using the sixth EEG recording in place of the first recording. In some embodiments, if the final intrinsic frequency (fIF) of the EEG recording obtained using the sixth EEG recording is > the predetermined amount outside the EEG band, a seventh EEG recording is obtained and the previously described method of determining a valid intrinsic frequency (vIF) of an EEG band of a subject (using a first EEG recording) is repeated using the seventh EEG recording in place of the first recording. In some embodiments, if the final intrinsic frequency (fIF) of the EEG recording obtained using the seventh EEG recording is > the predetermined amount outside the EEG band, an eighth EEG recording is obtained and the previously described method of determining a valid intrinsic frequency (vIF) of an EEG band of a subject (using a first EEG recording) is repeated using the eighth EEG recording in place of the first recording. In some embodiments, if the final intrinsic frequency (fIF) calculated using the third EEG recording is > the predetermined amount outside the EEG band, a range of final intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). In some embodiments, if the final intrinsic frequency (fIF) calculated using the third EEG recording is > the predetermined amount outside the EEG band, a range of final intrinsic frequencies (fIFs) of three or more of the first EEG recording, the second EEG recording, the third EEG recording, the fourth EEG recording, the fifth EEG recording, the sixth EEG recording, the seventh EEG recording, and the eighth EEG recording is calculated, wherein if the range is <2.0 Hz, then the mean value of the final intrinsic frequencies (fIFs) of the three or more of the first EEG recording, the second EEG recording, the third EEG recording, the fourth EEG recording, the fifth EEG recording, the sixth EEG recording, the seventh EEG recording, and the eighth EEG recording is determined to be the Valid intrinsic frequency (vIF).

In some embodiments of the method of determining a valid intrinsic frequency (vIF) of an EEG band of a subject, if a standard deviation (SD) of the N epoch IF values ≥0.75 Hz, or if the final intrinsic frequency (fIF) is > a predetermined amount outside the EEG band, wherein the predetermined amount is ±0.5 Hz, ±1.0 Hz, ±1.5 Hz, or ±2.0 Hz; then a second EEG recording is obtained and the previously described method of determining a valid intrinsic frequency (vIF) of an EEG band of a subject (using a first EEG recording) is repeated using the second EEG recording in place of the first EEG recording. In some embodiments, if a standard deviation (SD) of the N epoch IF values calculated using the second EEG reading ≥0.75 Hz, or if the final intrinsic frequency (fIF) calculated using the second EEG reading is > the predetermined amount outside the EEG band, then a third EEG recording is obtained and the previously described method of determining a valid intrinsic frequency (vIF) of an EEG band of a subject (using a first EEG recording) is repeated using the third EEG recording in place of the first EEG recording. In some embodiments, if a standard deviation (SD) of the N epoch IF values calculated using the third EEG reading ≥0.75 Hz, or if the final intrinsic frequency (fIF) calculated using the third EEG reading is > the predetermined amount outside the EEG band, then a fourth EEG recording is obtained and the previously described method of determining a valid intrinsic frequency (vIF) of an EEG band of a subject (using a first EEG recording) is repeated using the fourth EEG recording in place of the first EEG recording. In some embodiments, if a standard deviation (SD) of the N epoch IF values calculated using the fourth EEG reading ≥0.75 Hz, or if the final intrinsic frequency (fIF) calculated using the fourth EEG reading is > the predetermined amount outside the EEG band, then a fifth EEG recording is obtained and the previously described method of determining a valid intrinsic frequency (vIF) of an EEG band of a subject (using a first EEG recording) is repeated using the fifth EEG recording in place of the first EEG recording. In some embodiments, if a standard deviation (SD) of the N epoch IF values calculated using the fifth EEG reading ≥0.75 Hz, or if the final intrinsic frequency (fIF) calculated using the fifth EEG reading is > the predetermined amount outside the EEG band, then a sixth EEG recording is obtained and the method of claim 35 is repeated using the sixth EEG recording in place of the first EEG recording. In some embodiments, if a standard deviation (SD) of the N epoch IF values calculated using the sixth EEG reading ≥0.75 Hz, or if the final intrinsic frequency (fIF) calculated using the sixth EEG reading is > the predetermined amount outside the EEG band, then a seventh EEG recording is obtained and the previously described method of determining a valid intrinsic frequency (vIF) of an EEG band of a subject (using a first EEG recording) is repeated using the seventh EEG recording in place of the first EEG recording. In some embodiments, if a standard deviation (SD) of the N epoch IF values calculated using the seventh EEG reading ≥0.75 Hz, or if the final intrinsic frequency (fIF) calculated using the seventh EEG reading is > the predetermined amount outside the EEG band, then a eighth EEG recording is obtained and the previously described method of determining a valid intrinsic frequency (vIF) of an EEG band of a subject (using a first EEG recording) is repeated using the eighth EEG recording in place of the first EEG recording. In still further embodiments, if the final intrinsic frequency (fIF) calculated using the third EEG recording is > the predetermined amount outside the EEG band, or if the standard deviation (SD) of the N epoch IF values calculated using the third EEG reading ≥0.75 Hz, a range of final intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). Further still, in some embodiments, if the final intrinsic frequency (fIF) calculated using the eighth EEG recording is > the predetermined amount outside the EEG band or if the standard deviation (SD) of the N epoch IF values calculated using the eighth EEG reading ≥0.75 Hz, a range of final intrinsic frequencies (fIFs) of the at least three of the first EEG recording, the second EEG recording, the third EEG recording, the fourth EEG recording, the fifth EEG recording, the sixth EEG recording, the seventh EEG recording, the eighth EEG recording is calculated, wherein if the range is <2.0 Hz, then the mean value of the final intrinsic frequencies (fIFs) of the at least three of the first EEG recording, the second EEG recording, the third EEG recording, the fourth EEG recording, the fifth EEG recording, the sixth EEG recording, the seventh EEG recording, the eighth EEG recording is determined to be the Valid intrinsic frequency (vIF).

In some embodiments of the method of determining a valid intrinsic frequency (vIF) of an EEG band of a subject, if the final intrinsic frequency (fIF) is within the EEG band and the standard deviation (SD) of the N epoch IF value is <0.75 Hz, the final intrinsic frequency (fIF) is determined to be a valid intrinsic frequency (vIF). In some embodiments, a channel intrinsic frequency (cIF) is determined for each channel in the frequency domain epoch (i), and they are averaged to generate the epoch intrinsic frequency ($m_i$). In some embodiments, an epoch intrinsic frequency ($m_i$) is generated by averaging channel intrinsic frequencies (cIFs) generated from the channels meeting inclusion criteria and averaged together, wherein the inclusion criteria comprise: a greatest power in the EEG band as compared to all other channels of the EEG recording; a lowest variance as compared to all other channels of the EEG recording; or a highest Q-factor as compared to all other channels of the EEG recording.

Further still, in some embodiments, each channel from a multi-channel time domain EEG recording is treated separately and generates a channel intrinsic frequency (cIF) for each channel of the full time domain EEG recording, wherein a number of channel intrinsic frequencies (cIFs) is equal to the number of channels. In other embodiments, all channel intrinsic frequencies (cIFs) from a multi-channel time domain EEG recording are averaged together to obtain a representative intrinsic frequency (IF) of the time domain EEG recording. In some embodiments, a single channel intrinsic frequency (cIF) of a multi-channel time domain EEG recording comprises: a standard deviation (SD) below 0.75 Hz; the lowest (SD) of all the channel intrinsic frequencies (cIFs) of the multi-channel time domain EEG recording; and is selected as a representative intrinsic frequency (IF) for the time domain EEG recording. In still other embodiments, the channel intrinsic frequencies (cIFs) of all channels of a multi-channel time domain EEG recording that have a standard deviation (SD) below 0.75 Hz; are averaged together to obtain a representative intrinsic frequency (IF) of the multi-channel time domain EEG recording.

Provided herein is a device comprising a computer-implemented system configured to discriminate a valid intrinsic alpha frequency of at least one time domain EEG recording of a subject comprising a software module with a routine configured to: evaluate a first time domain EEG recording of a subject; determine if the time domain EEG recording has a stable intrinsic alpha frequency ($m_i$) throughout a plurality of epochs wherein a valid intrinsic alpha frequency comprises; a standard deviation between the epochs is <0.75 Hz, and a mean (M) of epoch intrinsic alpha frequencies ($m_i$) between 8.0 Hz to 13.0 Hz; set a final intrinsic alpha frequency (fIAF) equal to M; and output the final intrinsic alpha frequency (fIAF) to the device; or, label the first time domain EEG recording suspect; and continue to sequentially evaluate a plurality of subsequent time domain EEG recordings until a valid intrinsic alpha frequency can be obtained from a subsequent time domain EEG recording. In some embodiments of the computer implemented system, a total number of time domain EEG recordings is eight. In some embodiments of the computer implemented system, if the software module routine cannot obtain a valid intrinsic alpha frequency within the first time domain EEG recording, a second time domain EEG recording or a third time domain EEG recording, a range of epoch intrinsic alpha frequencies ($m_i$) of the first time domain EEG recording, the second time domain EEG recording and the third time domain EEG recording is calculated, wherein if the range is <2.0 Hz, the mean (M) of the first time domain EEG recording, the second time domain EEG recording and the third time domain EEG recording is calculated and is set equal to the final intrinsic alpha frequency (fIAF). In some embodiments of the computer implemented system, if the software module routine cannot obtain a valid intrinsic alpha frequency within eight time domain EEG recordings, the software module routine ends and outputs a message to a user that a valid intrinsic alpha frequency cannot be found. In some embodiments, the device comprises a Neuro-EEG Synchronization Therapy (NEST) device. In some embodiments, the device is configured to deliver low amplitude stimulation at an intrinsic alpha frequency that is the same as a patient's intrinsic alpha frequency.

Provided herein is a method of quantitatively analyzing EEG recordings to obtain a valid Intrinsic Alpha Frequency of a subject using a Neuro-EEG Synchronization Therapy (NEST) device comprising: obtaining a single 128-second time domain EEG recording; dividing the 128-second EEG recording into sixteen eight-second epochs; converting each epoch into a frequency domain epoch (i); calculating an epoch intrinsic alpha frequency ($m_i$) for each frequency domain epoch (i); successively eliminating the epoch intrinsic alpha frequencies ($m_i$) that are farthest from a mean, until the remaining epoch intrinsic alpha frequencies ($m_i$) are all within 0.5 Hz of the mean; and outputting a final intrinsic alpha frequency (fIAF) for the EEG recording that is equal to the mean value of the remaining epochs' epoch intrinsic alpha frequencies. In some embodiments, the final intrinsic alpha frequency (fIAF) is determined to be valid if the standard deviation of the epoch intrinsic alpha frequencies ($m_i$) from the epochs is <0.75 Hz and the final intrinsic alpha frequency (fIAF) is within the band of 8.0-13.0 Hz. In some embodiments, the final intrinsic alpha frequency (fIAF) is determined to be suspect if a standard deviation of the epoch intrinsic alpha frequencies ($m_i$) from the epochs is ≥0.75 Hz or the final intrinsic alpha frequency (fIAF) is outside the band of 8.0-13.0 Hz, and wherein a second EEG is recorded is obtained to determine if a valid intrinsic alpha frequency (vIAF) can be determined as defined previously, by replacing the single 128-second time domain EEG recording with the second EEG recording. In some embodiments, the final intrinsic alpha frequency (fIAF) using the second EEG recording is determined to be suspect if a standard deviation of the epoch intrinsic alpha frequencies ($m_i$) from the epochs is ≥0.75 Hz or the final intrinsic alpha frequency (fIAF) is outside the band of 8.0-13.0 Hz, and wherein a third EEG recording is obtained to determine if the valid intrinsic alpha frequency (vIAF) can be determined as defined previously, by replacing the single 128-second time domain EEG recording with the third EEG recording. In some embodiments, if the valid intrinsic alpha frequency (vIAF) cannot be obtained using the third EEG recording, a range of the final intrinsic alpha frequency (fIAF) values of the three previous EEG recordings is calculated, and if the range of the previous three final intrinsic alpha frequency (fIAF) values is <2.0 Hz, then the valid Intrinsic Alpha Frequency (vIAF) is set to the mean of the three previous final Intrinsic Alpha Frequencies (fIAFs).

In some embodiments of the method of determining a final intrinsic alpha frequency of a subject, wherein determining the farthest frequency domain epoch ($m_f$) from the mean M comprises calculating an index (I) of the frequency domain epoch that is farthest from the mean (M), wherein I=Index($max_i|m_i-M|$). In some embodiments of the method of determining a valid intrinsic frequency of an EEG band of a subject, wherein determining the farthest frequency domain epoch ($m_f$) from the mean M comprises calculating an index (I) of the frequency domain epoch that is farthest from the mean (M), wherein I=Index($max_i|m_i-M|$).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
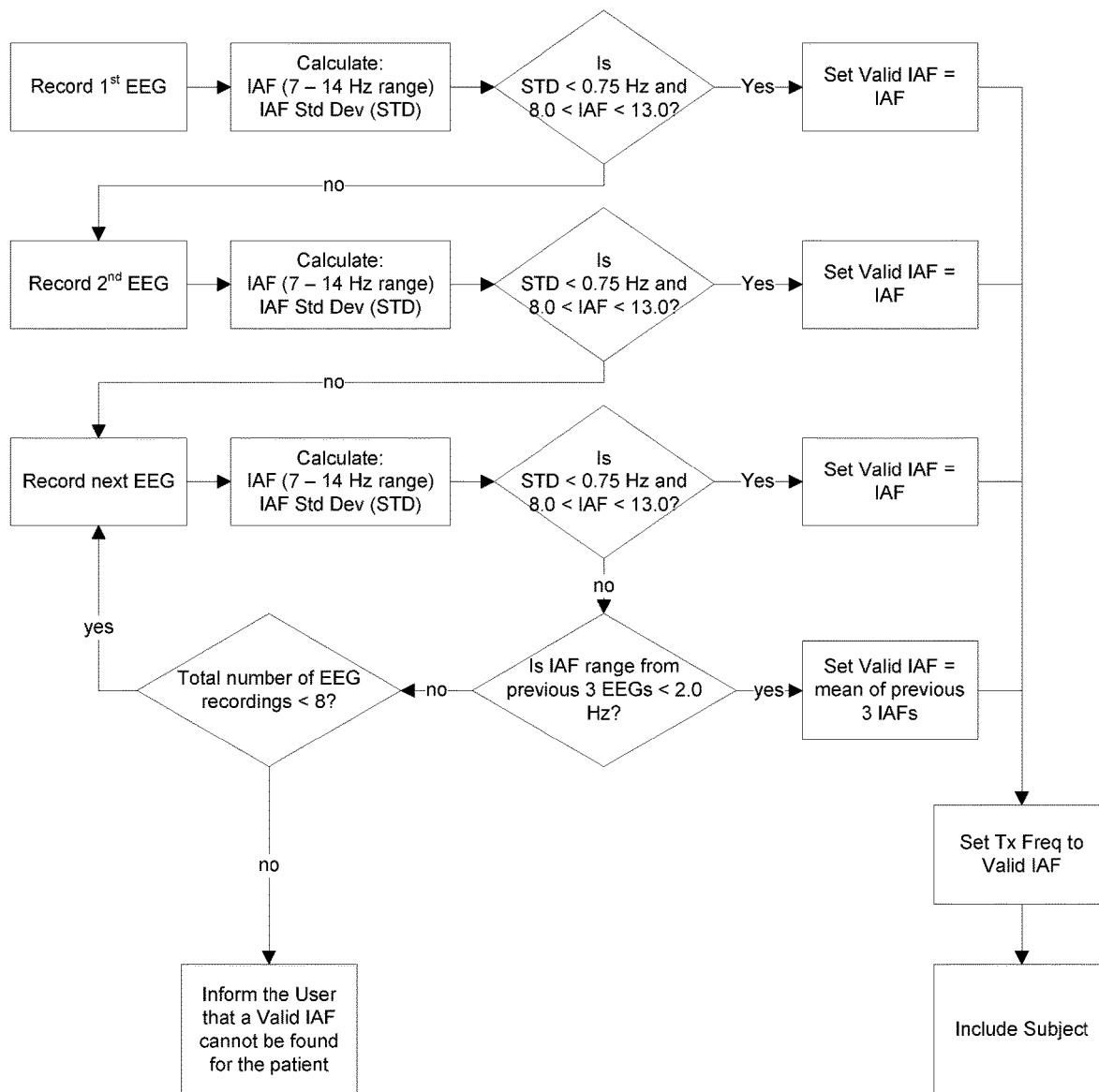
FIG. 1 is an illustrative flowchart of one aspect of the EEG Discrimination Algorithm

The present invention provides a novel method in which a subject's EEG is evaluated to either find a valid intrinsic alpha frequency (vIAF) or to require an additional recording. A subject's EEG is quantitatively analyzed with an algorithm by reviewing discreet epochs of an EEG, analyzing epoch IAFs of each epoch ($m_i$), successively pruning the values of these epoch IAFs until the remaining epoch-IAFs values are within a specific range of the mean. The final IAF estimate for that EEG is equal to the mean value of the remaining epochs' IAFs. This final IAF (fIAF) is utilized as a primary setting for Neuro-EEG Synchronization Therapy (NEST) Using Low Frequency Magnetic Stimulation with a NEST device. The NEST device is specifically tailored to deliver low amplitude stimulation at the patient's intrinsic alpha frequency (IAF).

The present invention describes an EEG algorithm to determine a valid IAF (vIAF). It is different, but, in part, derived from the IAF algorithm from U.S. Pat. No. 8,585,

568—SYSTEMS AND METHODS FOR NEURO-EEG-SYNCHRONIZATION THERAPY.

A recent published paper by Leuchter, et al. (2013) states that an effect on the symptoms of Major Depressive Disorder (MDD) will be obtained when the treatment frequency is delivered at the subject's IAF. In addition, a paper by Arns, et al. (2010) shows that using an rTMS pulse rate 1.0 Hz away from the subject's IAF does not result in significant benefit to the patient.

Therefore, it is imperative that a stable, repeatable IAF value be obtained. Thus in a clinical trial setting, subjects having an EEG of sufficient duration and quality that can be processed for quantitative analysis should be of primary interest for inclusion, and that a valid IAF can be obtained for each patient.

Described herein are methods and devices for utilizing an algorithm by which a valid intrinsic alpha frequency (vIAF) is determined by quantitatively analyzing EEG recordings one at a time to determine whether or not they are valid, and if necessary, requiring additional recordings until a valid EEG is found.

Provided herein is a method of determining a final intrinsic alpha frequency of a subject comprising: applying an EEG discrimination routine comprising: obtaining a first EEG recording in a time domain; dividing the first EEG recording into a plurality of epochs, each comprising a segment of data, wherein a total number of epochs is N; filtering the segment of data of each epoch using a high-pass filter; converting each epoch into a frequency domain epoch (i); filtering each frequency domain epoch (i) using a smoothing filter; calculating an epoch intrinsic alpha frequency ($m_i$) of each frequency domain epoch (i); calculating a mean (M) intrinsic alpha frequency (IAF) of all intrinsic alpha frequencies ($m_{i-N}$), wherein $$M = \frac{1}{N}\sum_{i=1}^{N} m_i;$$

determining a farthest frequency domain epoch ($m_f$) from the mean M, if $|m_f - M| > 0.5$ Hz, removing the farthest frequency domain epoch ($m_f$), decrementing N, and returning to step g), or if $|m_f - M| \leq 0.5$ Hz, continuing to next step; setting a final intrinsic alpha frequency (fIAF) equal to M; and outputting the final intrinsic alpha frequency (fIAF) to a user or to a device.

Disclosed herein, in various embodiments, are methods of determining a final intrinsic alpha frequency of a subject in a neuro-EEG synchronization therapy comprising: applying an EEG discrimination routine comprising: receiving a first EEG recording obtained from an EEG sensor in a time domain; segmenting the first EEG recording into a plurality of epochs, each comprising a segment of data, wherein a total number of epochs is N; filtering the segment of data of each epoch using a high-pass filter; converting each epoch into a frequency domain epoch (i); filtering each frequency domain epoch (i) using a smoothing filter; calculating an epoch intrinsic alpha frequency ($m_i$) of each frequency domain epoch (i); calculating a mean (M) intrinsic alpha frequency (IAF) of all intrinsic alpha frequencies ($m_{i-N}$), wherein $$M = \frac{1}{N}\sum_{i=1}^{N} m_i;$$

determining a farthest frequency domain epoch ($m_f$) from the mean M, if $|m_f - M| > 0.5$ Hz, removing the farthest frequency domain epoch ($m_f$), decrementing N, and returning to step g), or if $|m_f - M| \leq 0.5$ Hz, continuing to next step; setting a final intrinsic alpha frequency (fIAF) equal to M; and outputting the final intrinsic alpha frequency (fIAF) to a user or to a neuro-EEG synchronization therapy device; utilizing the final intrinsic alpha frequency (fIAF) in the neuro-EEG synchronization therapy. In some embodiments, the first EEG recording length is 128 seconds. In some embodiments, the first EEG recording is a single-channel recording. In some embodiments, the first EEG recording is a multi-channel recording, wherein an IAF estimate is made for each channel in an epoch and averaged together, or wherein each channel is treated separately, generating an IAF estimate for each channel for the full EEG recording, and wherein valid IAF estimates from each channel, as determined by step h), are averaged together to generate a final IAF. In some embodiments, a channel of the first EEG recording initially comprises 16 epochs. In some embodiments, the epoch intrinsic alpha frequency ($m_i$) of each frequency domain epoch (i) is calculated from 7.0 Hz to 14.0 Hz. In some embodiments, the final intrinsic alpha frequency (fIAF) is from 8.0 Hz to 13.0 Hz. In some embodiments, the first EEG recording comprises a sample rate of 128 samples/sec. In some embodiments, the high-pass filter comprises a $4^{th}$ order Butterworth IIR filter with the 3 dB cutoff set to 5.0 Hz. In some embodiments, the epoch intrinsic alpha frequency of each epoch ($m_i$) is determined using a Fast Fourier Transform (FFT). In some embodiments, the Fast Fourier Transform (FFT) uses a resolution of 1024 points, which results in a 0.125 Hz resolution per bin from 0 Hz to 64 Hz. In some embodiments, the Fast Fourier Transform (FFT) is smoothed with an averaging filter that averages the 5 points±2 from the target. In some embodiments, if a standard deviation (SD) of the N epoch IAF values ≥0.75 Hz, a second EEG recording is obtained and the method of claim 1 is repeated using the second EEG recording in place of the first EEG recording. In some embodiments, if a second standard deviation (SD) of the N epoch IAF values ≥0.75 Hz obtained using the second EEG recording, a third EEG recording is obtained and the method of claim 1 is repeated using the third EEG recording in place of the first EEG recording. In some embodiments, if a third standard deviation (SD) of the N epoch IAF values ≥0.75 Hz obtained using the third EEG recording, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF). In some embodiments, if the final intrinsic alpha frequency (fIAF) is <8.0 Hz or >13.0 Hz, a second EEG recording is obtained and the method of claim 1 is repeated using the second EEG recording in place of the first EEG recording. In some embodiments, if the final intrinsic alpha frequency (fIAF) calculated using the second EEG recording is <8.0 Hz or >13.0 Hz, a third EEG recording is obtained and the method of claim 1 is repeated using the third EEG recording in place of the first EEG recording. In some embodiments, if the final intrinsic alpha frequency (fIAF) calculated using the third EEG recording is <8.0 Hz or >13.0 Hz, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF). In some embodiments, if the final intrinsic alpha frequency (fIAF) of the EEG is from 8.0 Hz to 13.0 Hz and the standard deviation (SD) of the N epoch IAF values is <0.75 Hz, the final intrinsic alpha frequency (fIAF) is determined to be a valid intrinsic alpha frequency (vIAF). In some embodiments, if a standard deviation (SD) of the N epoch IAF values ≥0.75 Hz, or if the final intrinsic alpha frequency (fIAF) is <8.0 Hz or >13.0 Hz, then a second EEG recording is obtained and the method of claim 1 is repeated using the second EEG recording in place of the first EEG recording. In some embodiments, if a standard deviation (SD) of the N epoch IAF values calculated using the second EEG reading ≥0.75 Hz, or if the final intrinsic alpha frequency (fIAF) calculated using the second EEG reading is <8.0 Hz or >13.0 Hz, then a third EEG recording is obtained and the method of claim 1 is repeated using the third EEG recording in place of the first EEG recording. In some embodiments, if a standard deviation (SD) of the N epoch IAF values calculated using the third EEG reading ≥0.75 Hz, or if the final intrinsic alpha frequency (fIAF) calculated using the third EEG reading is <8.0 Hz or >13.0 Hz, then a fourth EEG recording is obtained and the method of claim 1 is repeated using the fourth EEG recording in place of the first EEG recording. In some embodiments, if a standard deviation (SD) of the N epoch IAF values calculated using the fourth EEG reading ≥0.75 Hz, or if the final intrinsic alpha frequency (fIAF) calculated using the fourth EEG reading is <8.0 Hz or >13.0 Hz, then a fifth EEG recording is obtained and the method of claim 1 is repeated using the fifth EEG recording in place of the first EEG recording. In some embodiments, if a standard deviation (SD) of the N epoch IAF values calculated using the fifth EEG reading ≥0.75 Hz, or if the final intrinsic alpha frequency (fIAF) calculated using the fifth EEG reading is <8.0 Hz or >13.0 Hz, then a sixth EEG recording is obtained and the method of claim 1 is repeated using the sixth EEG recording in place of the first EEG recording. In some embodiments, if a standard deviation (SD) of the N epoch IAF values calculated using the sixth EEG reading ≥0.75 Hz, or if the final intrinsic alpha frequency (fIAF) calculated using the sixth EEG reading is <8.0 Hz or >13.0 Hz, then a seventh EEG recording is obtained and the method of claim 1 is repeated using the seventh EEG recording in place of the first EEG recording. In some embodiments, if a standard deviation (SD) of the N epoch IAF values calculated using the seventh EEG reading ≥0.75 Hz, or if the final intrinsic alpha frequency (fIAF) calculated using the seventh EEG reading is <8.0 Hz or >13.0 Hz, then a eighth EEG recording is obtained and the method of claim 1 is repeated using the eighth EEG recording in place of the first EEG recording. In some embodiments, if the final intrinsic alpha frequency (fIAF) calculated using the third EEG recording is <8.0 Hz or >13.0 Hz or if the standard deviation (SD) of the N epoch IAF values calculated using the third EEG reading ≥0.75 Hz, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF). In some embodiments, if the final intrinsic alpha frequency (fIAF) calculated using the eighth EEG recording is <8.0 Hz or >13.0 Hz or if the standard deviation (SD) of the N epoch IAF values calcu-lated using the eighth EEG reading ≥0.75 Hz, a range of fIAF intrinsic alpha frequencies (fIAFs) of the at least three of the first EEG recording, the second EEG recording, the third EEG recording, the fourth EEG recording, the fifth EEG recording, the sixth EEG recording, the seventh EEG recording, the eighth EEG recording is calculated, wherein if the range is <2.0 Hz, then the mean value of the final intrinsic alpha frequencies (fIAFs) of at least three of the first EEG recording, the second EEG recording, the third EEG recording, the fourth EEG recording, the fifth EEG recording, the sixth EEG recording, the seventh EEG record-ing, the eighth EEG recording is determined to be the Valid intrinsic alpha frequency (vIAF). In some embodiments, a channel intrinsic alpha frequency is determined for each channel in the frequency domain epoch (i), and are averaged to generate the epoch intrinsic alpha frequency ($m_i$).

Disclosed herein, in various embodiments are methods of determining a final intrinsic alpha frequency of a subject in a neuro-EEG synchronization therapy comprising: applying an EEG discrimination routine comprising: obtaining a multi-channel EEG recording in a time domain; dividing the multi-channel EEG recording into a plurality of epochs, each epoch comprising a corresponding data segment from each channel, and averaging the data segments in each epoch together, wherein a total number of epochs is N; filtering the data segments of each epoch using a high-pass filter; con-verting each epoch into a frequency domain epoch (i); filtering each frequency domain epoch (i) using a smoothing filter; calculating an epoch intrinsic alpha frequency ($m_i$) of each frequency domain epoch (i); calculating a mean (M) intrinsic alpha frequency (IAF) of all intrinsic alpha fre-quencies ($m_{i-N}$), wherein $$M = \frac{1}{N}\sum_{i=1}^{N} m_i;$$

determining a farthest frequency domain epoch ($m_f$) from the mean M, if $|m_f-M|>0.5$ Hz, removing the farthest frequency domain epoch ($m_f$), decrementing N, and return-ing to step g), or if $|m_f-M|\leq 0.5$ Hz, continuing to next step; setting a final intrinsic alpha frequency (fIAF) equal to M; and outputting the final intrinsic alpha frequency (fIAF) to a user or to a device, wherein the device is configured to conduct the neuro-EEG synchronization therapy. In some embodiments, the epoch intrinsic alpha frequency ($m_i$) is generated by averaging channel intrinsic alpha frequencies generated from the channels meeting inclusion criteria and averaged together, wherein the inclusion criteria comprise: a greatest alpha power as compared to all other channels of the EEG recording; a lowest variance as compared to all other channels of the EEG recording; or a highest Q-factor as compared to all other channels of the EEG recording.

Disclosed herein, in various embodiments are methods of determining a final intrinsic alpha frequency of a subject in a neuro-EEG synchronization therapy comprising: applying an EEG discrimination routine comprising: obtaining a multi-channel EEG recording from an EEG sensor in a time domain; treating each channel separately, dividing each channel of the multi-channel EEG recording into a plurality of epochs, each epoch comprising a data segment from each channel, wherein a total number of epochs for each channel is N; filtering the data segments of each epoch, of each channel, using a high-pass filter; converting each epoch, of each channel, into a frequency domain epoch (i); filtering each frequency domain epoch (i), of each channel, using a smoothing filter; calculating an epoch intrinsic alpha frequency ($m_i$) of each frequency domain epoch (i) for each channel; calculating a mean (M) channel intrinsic alpha frequency (cIAF) of all intrinsic alpha frequencies ($m_{i-N}$) for each channel, wherein $$M = \frac{1}{N}\sum_{i=1}^{N} m_i;$$

determining a farthest frequency domain epoch ($m_f$) from the mean M for each channel, if $|m_f-M|>0.5$ Hz, removing the farthest frequency domain epoch ($m_f$), decrementing N, and returning to step g), or if $|m_f-M|\leq 0.5$ Hz, continuing to next step; averaging the mean (M) channel intrinsic alpha frequency (cIAF) of all channels to determine a final intrinsic alpha frequency (fIAF); setting a final intrinsic alpha frequency (fIAF) equal to M for the entire multi-channel EEG recording; and outputting the final intrinsic alpha frequency (fIAF) to a user or to a device, wherein the device is configured to conduct the neuro-EEG synchronization therapy. In some embodiments, a single channel intrinsic alpha frequency (cIAF) of the multi-channel EEG recording comprises; a frequency band between 8.0 Hz-13.0 Hz; a standard deviation (SD) below 0.75 Hz; the lowest (SD) of all the channel intrinsic alpha frequencies (cIAFs) of the multi-channel EEG recording; and the single channel intrinsic alpha frequency (cIAF) is selected as a representative intrinsic alpha frequency (IAF) for the multi-channel EEG recording. In some embodiments, the intrinsic channel alpha frequencies (cIAFs) of all channels of the multi-channel EEG recording that are within a band between 8.0 Hz-13.0 Hz and have a standard deviation (SD) below 0.75 Hz, are averaged together to obtain a representative intrinsic alpha frequency (IAF) of the multi-channel time domain EEG recording.

Disclosed herein, in various embodiments are methods of determining a valid intrinsic frequency of an EEG band of a subject in neuro-EEG synchronization therapy comprising: applying an EEG discrimination routine comprising: obtaining a first EEG recording in a time domain; dividing the first EEG recording into a plurality of epochs, wherein a total number of epochs is N; filtering the data using a high-pass filter; converting each epoch into a frequency domain epoch (i); filtering each frequency domain epoch (i) using a smoothing filter; calculating an epoch intrinsic frequency ($m_i$) in an EEG band of each frequency domain epoch (i); calculating a mean (M) intrinsic frequency (IF) in the EEG band of all epoch intrinsic frequencies ($m_{i-N}$), wherein $$M = \frac{1}{N}\sum_{i=1}^{N} m_i;$$

determining a farthest frequency domain epoch ($m_f$) from the mean, if $|m_f-M|>0.5$ Hz, removing the farthest frequency domain epoch ($m_f$), decrementing N, and returning to step g), or if $|m_f-M|\leq 0.5$ Hz, continuing to next step; setting a final intrinsic frequency (fIF) in the EEG band equal to M; and outputting the final intrinsic frequency (fIF) in the EEG band to a user or device, wherein the device is configured to conduct the neuro-EEG synchronization therapy. In some embodiments, the EEG band comprises one or more selected from: an Alpha band; a Theta band; a Beta band; a Gamma band; and a Delta band. In some embodiments, the EEG recording length is 128 seconds. In some embodiments, the EEG recording is a single-channel recording. In some embodiments, the EEG recording is a multi-channel recording, wherein a channel intrinsic frequency (cIF) estimate is made for each channel in an epoch and averaged together, or wherein each channel is treated separately, generating a final intrinsic frequency (fIF) estimate for each channel for the full EEG recording, and wherein final intrinsic frequency estimates from each channel, as determined by step h), are averaged together to generate a final intrinsic frequency (fIF). In some embodiments, a channel of the EEG recording comprises 16 epochs. In some embodiments, the calculated epoch intrinsic frequency ($m_i$) of the EEG comprises a range that is at least: ±0.5 Hz outside a range of the EEG band; ±1.0 Hz outside the range of the EEG band; ±1.5 Hz outside the range of the EEG band; and ±2.0 Hz outside the range of the EEG band. In some embodiments, the EEG recording comprises a sample rate of 128 samples/sec. In some embodiments, the high-pass filter uses a $4^{th}$ order Butterworth IIR filter with the 3 dB cutoff set to 5.0 Hz. In some embodiments, the epoch intrinsic alpha frequency of each epoch ($m_i$) is determined using a Fast Fourier Transform (FFT). In some embodiments, the Fast Fourier Transform (FFT) uses a resolution of 1024 points, which results in a 0.125 Hz resolution per bin from 0 Hz to 64 Hz. In some embodiments, the Fast Fourier Transform (FFT) is smoothed with an averaging filter that averages 5 points±2 from the target. In some embodiments, if the standard deviation (SD) of the N epoch IF values $\geq 0.75$ Hz, a second EEG recording is obtained and the method of claim 35 is repeated using the second EEG recording in place of the first EEG recording. In some embodiments, if the standard deviation (SD) of the N epoch IF values calculated using the second EEG recording is $\geq 0.75$ Hz, a third EEG recording is obtained and the method of claim 35 is repeated using the third EEG recording in place of the first EEG recording. In some embodiments, if the standard deviation (SD) of the N epoch IF values calculated using the third EEG recording is $\geq 0.75$ Hz, a fourth EEG recording is obtained and the method of claim 35 is repeated using the fourth EEG recording in place of the first EEG recording. In some embodiments, if the standard deviation (SD) of the N epoch IF values calculated using the fourth EEG recording is $\geq 0.75$ Hz, a fifth EEG recording is obtained and the method of claim 35 is repeated using the fifth EEG recording in place of the first EEG recording. In some embodiments, if the standard deviation (SD) of the N epoch IF values calculated using the fifth EEG recording is $\geq 0.75$ Hz, a sixth EEG recording is obtained and the method of claim 35 is repeated using the sixth EEG recording in place of the first EEG recording. In some embodiments, if the standard deviation (SD) of the N epoch IF values calculated using the sixth EEG recording is $\geq 0.75$ Hz, a seventh EEG recording is obtained and the method of claim 35 is repeated using the seventh EEG recording in place of the first EEG recording. In some embodiments, if the standard deviation (SD) of the N epoch IF values calculated using the seventh EEG recording is $\geq 0.75$ Hz, an eighth EEG recording is obtained and the method of claim 35 is repeated using the eighth EEG recording in place of the first EEG recording. In some embodiments, if an eighth standard deviation (SD) of the N epoch IF values $\geq 0.75$ Hz obtained using the eighth EEG recording, a range of fIF intrinsic frequencies (fIFs) of at least three of the first EEG recording, the second EEG recording, the third EEG recording, the fourth EEG recording, the fifth EEG recording, the sixth EEG recording, the seventh EEG recording, and the eighth EEG recording is calculated, wherein if the range is <2.0 Hz, then the mean value of the final intrinsic frequencies (fIFs) of at least three of the first EEG recording, the second EEG recording, the third EEG recording, the fourth EEG recording, the fifth EEG recording, the sixth EEG recording, the seventh EEG recording, and the eighth EEG recording is determined to be the Valid intrinsic frequency (vIF). In some embodiments, if a third standard deviation (SD) of the N epoch IF values ≥0.75 Hz obtained using the third EEG recording, a range of fIF intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). In some embodiments, if the final intrinsic frequency (fIF) of the EEG recording is > a predetermined amount outside the EEG band, a second EEG recording is obtained and the method of claim 35 is repeated using the second EEG recording in place of the first EEG recording. In some embodiments, the predetermined amount is: ±0.5 Hz; ±1.0 Hz; ±1.5 Hz; or ±2.0 Hz. In some embodiments, if the final intrinsic frequency (fIF) of the EEG recording obtained using the second EEG recording is > the predetermined amount outside the EEG band, a third EEG recording is obtained and the method of claim 35 is repeated using the third EEG recording in place of the first EEG recording. In some embodiments, if the final intrinsic frequency (fIF) of the EEG recording obtained using the third EEG recording is > the predetermined amount outside the EEG band, a fourth EEG recording is obtained and the method of claim 35 is repeated using the fourth EEG recording in place of the first EEG recording. In some embodiments, if the final intrinsic frequency (fIF) of the EEG recording obtained using the fourth EEG recording is > the predetermined amount outside the EEG band, a fifth EEG recording is obtained and the method of claim 35 is repeated using the fifth EEG recording in place of the first EEG recording. In some embodiments, if the final intrinsic frequency (fIF) of the EEG recording obtained using the fifth EEG recording is > the predetermined amount outside the EEG band, a sixth EEG recording is obtained and the method of claim 35 is repeated using the sixth EEG recording in place of the first EEG recording. In some embodiments, if the final intrinsic frequency (fIF) of the EEG recording obtained using the sixth EEG recording is > the predetermined amount outside the EEG band, a seventh EEG recording is obtained and the method of claim 35 is repeated using the seventh EEG recording in place of the first EEG recording. In some embodiments, if the final intrinsic frequency (fIF) of the EEG recording obtained using the seventh EEG recording is > the predetermined amount outside the EEG band, an eighth EEG recording is obtained and the method of claim 35 is repeated using the eighth EEG recording in place of the first EEG recording. In some embodiments, if the final intrinsic frequency (fIF) calculated using the third EEG recording is > the predetermined amount outside the EEG band, a range of fIF intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). In some embodiments, if the final intrinsic frequency (fIF) calculated using the third EEG recording is > the predetermined amount outside the EEG band, a range of fIF intrinsic frequencies (fIFs) of three or more of the first EEG recording, the second EEG recording, the third EEG recording, the fourth EEG recording, the fifth EEG recording, the sixth EEG recording, the seventh EEG recording, and the eighth EEG recording is calculated, wherein if the range is <2.0 Hz, then the mean value of the final intrinsic frequencies (fIFs) of three of the first EEG recording, the second EEG recording, the third EEG recording, the fourth EEG recording, the fifth EEG recording, the sixth EEG recording, the seventh EEG recording, and the eighth EEG recording is determined to be the Valid intrinsic frequency (vIF). In some embodiments, if a standard deviation (SD) of the N epoch IF values ≥0.75 Hz, or if the final intrinsic frequency (fIF) is > a predetermined amount outside the EEG band, wherein the predetermined amount is ±0.5 Hz, ±1.0 Hz, ±1.5 Hz, or ±2.0 Hz; then a second EEG recording is obtained and the method of claim 35 is repeated using the second EEG recording in place of the first EEG recording. In some embodiments, if a standard deviation (SD) of the N epoch IF values calculated using the second EEG reading ≥0.75 Hz, or if the final intrinsic frequency (fIF) calculated using the second EEG reading is > the predetermined amount outside the EEG band, then a third EEG recording is obtained and the method of claim 35 is repeated using the third EEG recording in place of the first EEG recording. In some embodiments, if a standard deviation (SD) of the N epoch IF values calculated using the third EEG reading ≥0.75 Hz, or if the final intrinsic frequency (fIF) calculated using the third EEG reading is > the predetermined amount outside the EEG band, then a fourth EEG recording is obtained and the method of claim 35 is repeated using the fourth EEG recording in place of the first EEG recording. In some embodiments, if a standard deviation (SD) of the N epoch IF values calculated using the fourth EEG reading ≥0.75 Hz, or if the final intrinsic frequency (fIF) calculated using the fourth EEG reading is > the predetermined amount outside the EEG band, then a fifth EEG recording is obtained and the method of claim 35 is repeated using the fifth EEG recording in place of the first EEG recording. In some embodiments, if a standard deviation (SD) of the N epoch IF values calculated using the fifth EEG reading ≥0.75 Hz, or if the final intrinsic frequency (fIF) calculated using the fifth EEG reading is > the predetermined amount outside the EEG band, then a sixth EEG recording is obtained and the method of claim 35 is repeated using the sixth EEG recording in place of the first EEG recording. In some embodiments, if a standard deviation (SD) of the N epoch IF values calculated using the sixth EEG reading ≥0.75 Hz, or if the final intrinsic frequency (fIF) calculated using the sixth EEG reading is > the predetermined amount outside the EEG band, then a seventh EEG recording is obtained and the method of claim 35 is repeated using the seventh EEG recording in place of the first EEG recording. In some embodiments, if a standard deviation (SD) of the N epoch IF values calculated using the seventh EEG reading ≥0.75 Hz, or if the final intrinsic frequency (fIF) calculated using the seventh EEG reading is > the predetermined amount outside the EEG band, then a eighth EEG recording is obtained and the method of claim 35 is repeated using the eighth EEG recording in place of the first EEG recording. In some embodiments, if the final intrinsic frequency (fIF) calculated using the third EEG recording is > the predetermined amount outside the EEG band, or if the standard deviation (SD) of the N epoch IF values calculated using the third EEG reading ≥0.75 Hz, a range of fIF intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). In some embodiments, if the final intrinsic frequency (fIF) calculated using the eighth EEG recording is > the predetermined amount outside the EEG band or if the standard deviation (SD) of the N epoch IF values calculated using the eighth EEG reading ≥0.75 Hz, a range of fIF intrinsic frequencies (fIFs) of the at least three of the first EEG recording, the second EEG recording, the third EEG recording, the fourth EEG recording, the fifth EEG recording, the sixth EEG recording, the seventh EEG recording, the eighth EEG recording is calculated, wherein if the range is <2.0 Hz, then the mean value of the final intrinsic frequencies (fIFs) of at least three of the first EEG recording, the second EEG recording, the third EEG recording, the fourth EEG recording, the fifth EEG recording, the sixth EEG recording, the seventh EEG recording, the eighth EEG recording is determined to be the Valid intrinsic frequency (vIF). In some embodiments, if the final intrinsic frequency (fIF) is within the EEG band and the standard deviation (SD) of the N epoch IF values is <0.75 Hz, the final intrinsic frequency (fIF) is determined to be a valid intrinsic frequency (vIF). In some embodiments, a channel intrinsic frequency is determined for each channel in the frequency domain epoch (i), and are averaged to generate the epoch intrinsic frequency ($m_i$). In some embodiments, an epoch intrinsic frequency ($m_i$) is generated by averaging channel intrinsic frequencies generated from the channels meeting inclusion criteria and averaged together, wherein the inclusion criteria comprise: a greatest power in the EEG band as compared to all other channels of the EEG recording; a lowest variance as compared to all other channels of the EEG recording; or a highest Q-factor as compared to all other channels of the EEG recording. In some embodiments, each channel from a multi-channel time domain EEG recording is treated separately and generates a channel intrinsic frequency (cIF) for each channel of the multi-channel time domain EEG recording, wherein a number of channel intrinsic frequencies (cIFs) is equal to the number of channels. In some embodiments, all channel intrinsic frequencies (cIFs) from a multi-channel time domain EEG recording are averaged together to obtain a representative intrinsic frequency (IF) of the multi-channel time domain EEG recording. In some embodiments, a single channel intrinsic frequency (cIF) of a multi-channel time domain EEG recording comprises: a standard deviation (SD) below 0.75 Hz; the lowest (SD) of all the channel intrinsic frequencies (cIFs) of the multi-channel time domain EEG recording; and the single channel intrinsic frequency (cIF) is selected as a representative intrinsic frequency (IF) for the multi-channel time domain EEG recording. In some embodiments, the channel intrinsic frequency (cIF) of all channels of a multi-channel time domain EEG recording that have a standard deviation (SD) below 0.75 Hz; are averaged together to obtain a representative intrinsic frequency (IF) of the multi-channel time domain EEG recording. Disclosed herein, in various embodiments, are computer-implemented systems for determining an intrinsic alpha frequency of a subject comprising: an input device configured to receive a first time domain EEG recording of a subject, wherein the EEG recording is obtained from an EEG sensor external to the computer-implemented system; a digital processing device comprising an operating system configured to perform executable instructions and a memory; a computer program including instructions executable by the digital processing device configured to discriminate a valid intrinsic alpha frequency of at least one time domain EEG recording of a subject comprising a software module configured to: determine if the time domain EEG recording has a stable intrinsic alpha frequency ($m_i$) throughout a plurality of epochs, wherein a valid intrinsic alpha frequency comprises: a standard deviation between the epochs <0.75 Hz, and a mean (M) of epoch intrinsic alpha frequencies ($m_i$) between 8.0 Hz to 13.0 Hz, set a final intrinsic alpha frequency (fIAF) equal to M; output the final intrinsic alpha frequency (fIAF) to a device, or, label the first time domain EEG recording suspect, and continue to sequentially evaluate a plurality of subsequent time domain EEG recordings until a valid intrinsic alpha frequency is be obtained from a subsequent time domain EEG recording, wherein the plurality of subsequent time domain EEG recording are obtained from an EEG sensor external to the computer-implemented system. In some cases, a total number of time domain EEG recordings is eight. In some cases, if the software module routine cannot obtain a valid intrinsic alpha frequency within the first time domain EEG recording, a second time domain EEG recording or a third time domain EEG recording, a range of epoch intrinsic alpha frequencies ($m_i$) of the first time domain EEG recording, the second time domain EEG recording and the third time domain EEG recording is calculated, wherein if the range is <2.0 Hz, the mean (M) of the first time domain EEG recording, the second time domain EEG recording and the third time domain EEG recording is calculated and is set equal to the final intrinsic alpha frequency (fIAF). In some cases, if the software module routine cannot obtain a valid intrinsic alpha frequency within eight time domain EEG recordings, the software module routine ends and outputs a message to a user that a valid intrinsic alpha frequency cannot be found. In some cases, the device is a Neuro-EEG Synchronization Therapy (NEST) device. In some cases, the device is configured to deliver low amplitude stimulation at an intrinsic alpha frequency that is the same as a patient's intrinsic alpha frequency.

Disclosed herein, in various embodiments are methods of quantitatively analyzing EEG recordings to obtain a valid Intrinsic Alpha Frequency of a subject using a Neuro-EEG Synchronization Therapy (NEST) device comprising: obtaining a single 128-second time domain EEG recording from an EEG sensor external to the device; dividing the 128-second EEG recording into sixteen eight-second epochs; converting each epoch into a frequency domain epoch (i); calculating an epoch intrinsic alpha frequency ($m_i$) for each frequency domain epoch (i); and successively eliminating the epoch intrinsic alpha frequencies ($m_i$) that are farthest from a mean, until the remaining epoch intrinsic alpha frequencies ($m_i$) are all within 0.5 Hz of the mean; and outputting a final intrinsic alpha frequency (fIAF) for the EEG recording that is equal to the mean value of the remaining epochs' epoch intrinsic alpha frequencies. In some cases, the final intrinsic alpha frequency (fIAF) is determined to be valid if a standard deviation of the epoch intrinsic alpha frequencies ($m_i$) from the epochs is <0.75 Hz and the final intrinsic alpha frequency (fIAF) within the band of 8.0-13.0 Hz. In some cases, the final intrinsic alpha frequency (fIAF) is determined to be suspect if a standard deviation of the epoch intrinsic alpha frequencies ($m_i$) from the epochs is ≥0.75 Hz or the final intrinsic alpha frequency (fIAF) is outside the band of 8.0-13.0 Hz, and wherein a second EEG recording is obtained to determine if a valid intrinsic alpha frequency (vIAF) can be determined by repeating the steps of claim 88 replacing the single 128- second time domain EEG recording with the second EEG recording. In some cases, the final intrinsic alpha frequency (fIAF) using the second EEG recording is determined to be suspect if a standard deviation of the epoch intrinsic alpha frequencies ($m_i$) from the epochs is ≥0.75 Hz or the final intrinsic alpha frequency (fIAF) is outside the band of 8.0-13.0 Hz, and wherein a third EEG recording is obtained to determine if the valid intrinsic alpha frequency (vIAF) can be determined by repeating the steps of claim 88 replacing the single 128-second time domain EEG recording with the third EEG recording. In some cases, if the valid intrinsic alpha frequency (vIAF) cannot be obtained using the third EEG recording, a range of the final intrinsic alpha frequency (fIAF) values of the three previous EEG recordings is calculated, and if the range of the previous three final intrinsic alpha frequency (fIAF) values is <2.0 Hz, then the valid Intrinsic Alpha Frequency (vIAF) is set to the mean of the three previous final Intrinsic Alpha Frequencies (fIAFs). In some cases, determining the farthest frequency domain epoch ($m_f$) from the mean M comprises calculating an index (I) of the frequency domain epoch that is farthest from the mean (M), wherein I=Index($\max_i |m_i - M|$). In some cases, determining the farthest frequency domain epoch ($m_f$) from the mean M comprises calculating an index (I) of the frequency domain epoch that is farthest from the mean (M), wherein I=Index($\max_i |m_i - M|$). In some embodiments, wherein determining a farthest frequency domain epoch ($m_f$) from the mean M comprises calculating an index (I) of the frequency domain epoch that is farthest from the mean (M), wherein I=Index($\max_i |m_i - M|$).

As described above, an IAF estimate is created based on a frequency analysis of the EEG. The EEG recording is divided into 8-second epochs. An IAF estimate is made for each epoch, resulting in a number of discreet epoch-IAF values. A routine performs successive pruning of these values by eliminating the farthest from the mean, until the remaining epoch-IAF values were all within 0.5 Hz of the mean. The final IAF estimate for that EEG is equal to the mean value of the remaining epochs' IAFs.

In some embodiments, the first EEG recording length is 128 seconds. In some embodiments, the first EEG recording is a single-channel recording. In some embodiments, the first EEG recording is a multi-channel recording, wherein an IAF estimate is made for each channel in an epoch and averaged together, or wherein each channel is treated separately, generating an IAF estimate for each channel for the full EEG recording, and wherein valid IAF estimates from each channel, as determined by the step; determining a farthest frequency domain epoch ($m_f$) from the mean M, if $|m_f - M| > 0.5$ Hz, removing the farthest frequency domain epoch ($m_f$), decrementing N, and returning to step g), or if $|m_f - M| ≤ 0.5$ Hz, are averaged together to generate a final IAF. In some embodiments, a channel of the first EEG recording initially comprises 16 epochs. In some embodiments, the epoch intrinsic alpha frequency ($m_i$) of each frequency domain epoch (i) is calculated from 7.0 Hz to 14.0 Hz. In some embodiments, the final intrinsic alpha frequency (fIAF) is from 8.0 Hz to 13.0 Hz. In some embodiments, the first EEG recording comprises a sample rate of 128 samples/sec. In some embodiments, the high-pass filter comprises a $4^{th}$ order Butterworth IIR filter with the 3 dB cutoff set to 5.0 Hz. In some embodiments, the epoch intrinsic alpha frequency of each epoch ($m_i$) is determined using a Fast Fourier Transform (FFT). In some embodiments, the Fast Fourier Transform (FFT) uses a resolution of 1024 points, which results in a 0.125 Hz resolution per bin from 0 Hz to 64 Hz.

In some embodiments, the Fast Fourier Transform (FFT) is smoothed with an averaging filter that averages the 5 points±2 from the target.

As described above, a final IAF estimate for an EEG recording is equal to the mean value of the remaining epoch's IAFs (following successive pruning) In order to accomplish this, an IAF estimate of each epoch must be calculated. In the following example, a typical EEG is 128 seconds and is divided in 16 8-second epochs, and each single recorded EEG epoch input data is analyzed as follows. A filter is applied to the data of the epoch. The sample rate is 128 samples/sec. The filtering uses a $4^{th}$ order Butterworth IIR filter with the 3 dB cutoff set to 5.0 Hz. Next the data is run through a Fast Fourier Transform (FFT) to convert the data from a sequence to frequency. The FFT uses 1024 points, which results in a 0.125 Hz resolution per bin over the range of 0-64 Hz. A single smoothing filter is used on the FFT to remove spurious peaks. This is a simple averaging filter that averages the 5 points+/-2 from the target. The data is analyzed to determine the peak location of the FFT between 7.0 Hz and 14.0 Hz. The peak IAF estimate of the epoch is equal to the frequency of that peak.

It should be noted, the peak IAF estimates are found in the range from 7.0-14.0 Hz. However, the Alpha band is 8.0-13.0 Hz. The EEG discrimination algorithm will label an IAF estimate as "suspect" if it is out of band. To determine if an estimate is out of band, the range to find peak IAF estimates must be wider than the Alpha band. For this example of the algorithm a window 1.0 Hz outside the Alpha band was chosen. However, depending on the band being analyzed, a different window may be chosen.

As noted previously, outliers are identified and discarded in order to determine a final IAF estimate. Alpha waves tend to be bursty in an EEG, with large sections showing little to no alpha activity, followed by a rhythmic section with significant alpha peaks. After sixteen 8-second epochs have been processed to obtain 16 IAF estimates, the algorithm removes outliers, which are most likely due to noise. A routine performs successive pruning of these values by eliminating the farthest from the mean, until the remaining epoch-IAF values are all within 0.5 Hz of the mean. The sequence below gives the specifics of the routine. In this, N is the total number of remaining epochs after pruning. M is the mean of the IAFs for all remaining epochs. $m_i$ is the IAF estimate for epoch i. The routine is described as follows: Set N to 16; the mean of the IAFs for all remaining epochs is calculated using the following formula:

$$M = \frac{1}{N}\sum_{i=1}^{N} m_i;$$

Next, the Index, I, of the farthest epoch from the mean is calculated, wherein I=Index($\max_i |m_i - M|$); and If $|m_I - M| > 0.5$ Hz, then the farthest epoch is removed, the value N is decreased by 1, and the process is repeated by recalculating the mean of the IAFs for all remaining epochs, again using the formula:

$$M = \frac{1}{N}\sum_{i=1}^{N} m_i.$$

This routine is repeated until the remaining epoch-IAF values are all within 0.5 Hz of the mean. Once this condition is met, the IAF estimate for the EEG is set equal to M.

As described herein, the Index (I) is the frequency domain epoch number (1 ... N) in any iteration of the time domain EEG. During pruning, the algorithm finds the index (I) of the epoch (1 ... N) where the epoch IAF is farthest from the mean M. If this difference is greater than 0.5 Hz, the epoch is discarded and N is decreased. For example, if one begins with the following 16 epochs: (1, 2, 3, 4, 5, 6, 7, 8, 9, 10, 11, 12, 13, 14, 15, 16); and then find that epoch #6 is farthest from the mean (i.e., I=6), and is also greater than 0.5 Hz, epoch #6 would be discarded, so the new list will be: (1, 2, 3, 4, 5, ___ 7, 8, 9, 10, 11, 12, 13, 14, 15, 16), and N is decreased by 1.

The remaining epochs are then renumbered, resulting in (1, 2, 3, 4, 5, 6, 7, 8, 9, 10, 11, 12, 13, 14, 15). The routine performs successive pruning of these values until the remaining epoch-IAF values were all within 0.5 Hz of the mean. Quite conceivably, one could wind up removing the same index in two iterations of the pruning routine. For example, utilizing the previous result: The $6^{th}$ epoch (Index=6) is again found to be farthest from the mean. It is again removed: (1, 2, 3, 4, 5, ___ 7, 8, 9, 10, 11, 12, 13, 14, 15); and the remaining epochs are again renumbered: 1, 2, 3, 4, 5, 6, 7, 8, 9, 10, 11, 12, 13, 14). This process would continue until the remaining epoch-IAF values were all within 0.5 Hz of the mean.

The purpose of the discrimination routine is to find a stable, repeatable IAF. Such an IAF is referred to as a "Valid" IAF. If an EEG recording results in a final IAF (fIAF) that is either highly variable throughout the 16 epochs (standard deviation of the N epoch IAFs is greater than or equal to 0.75 Hz), or the fIAF is out of band (8.0-13.0 Hz), it is labeled as "suspect", and another EEG may be required.

If the first EEG results in a Valid IAF, the routine ends and the treatment frequency is set to that value. If not, a second EEG recording is performed to see if that one results in a Valid IAF. If that IAF is suspect, a $3^{rd}$ EEG is recorded.

In some embodiments, if a standard deviation (SD) of the N epoch IAF values ≥0.75 Hz, a second EEG recording is obtained and the previously described method of determining a final intrinsic alpha frequency of a subject (using a first EEG recording) is repeated using the second EEG recording in place of the first EEG recording. In some embodiments, if a second standard deviation (SD) of the N epoch IAF values ≥0.75 Hz obtained using the second EEG recording, a third EEG recording is obtained and the previously described method of determining a final intrinsic alpha frequency of a subject (using a first EEG recording) is repeated using the third EEG recording in place of the first EEG recording.

After the $3^{rd}$ EEG, an additional option is available to find a Valid IAF. It has been found that, even if the IAFs are highly variable (standard deviation of the 16 epochs is greater than or equal to 0.75 Hz), many times the final IAFs of consecutive EEG recordings are still close to the same value. Therefore, after the $3^{rd}$ EEG, the range of fIAF values of the previous 3 EEGs is calculated, and if that range is less than 2.0 Hz, then the Valid IAF is set to the mean of the 3 suspect fIAFs. In some embodiments, if a third standard deviation (SD) of the N epoch IAF values ≥0.75 Hz obtained using the third EEG recording, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF).

In still other embodiments, if the final intrinsic alpha frequency (fIAF) is <8.0 Hz or >13.0 Hz, a second EEG recording is obtained and the previously described method of determining a final intrinsic alpha frequency of a subject (using a first EEG recording) is repeated using the second EEG recording in place of the first EEG recording. In still other embodiments, if the final intrinsic alpha frequency (fIAF) calculated using the second EEG recording is <8.0 Hz or >13.0 Hz, a third EEG recording is obtained and the previously described method of determining a final intrinsic alpha frequency of a subject (using a first EEG recording) is repeated using the third EEG recording in place of the first EEG recording. In still other embodiments, if the final intrinsic alpha frequency (fIAF) calculated using the third EEG recording is <8.0 Hz or >13.0 Hz, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF). Still further, in other embodiments, if the final intrinsic alpha frequency (fIAF) of the EEG is from 8.0 Hz-13.0 Hz and the standard deviation (SD) of the N epoch IAF values is <0.75 Hz, the final intrinsic alpha frequency (fIAF) is determined to be a valid intrinsic alpha frequency (vIAF).

In some embodiments of the method of determining a final intrinsic alpha frequency of a subject; if a standard deviation (SD) of the N epoch IAF values ≥0.75 Hz, or if the final intrinsic alpha frequency (fIAF) is <8.0 Hz or >13.0 Hz, then a second EEG recording is obtained and the previously described method of determining a final intrinsic alpha frequency of a subject (using a first EEG recording) is repeated using the second EEG recording in place of the first EEG recording. In some embodiments, if a standard deviation (SD) of the N epoch IAF values calculated using the second EEG reading ≥0.75 Hz, or if the final intrinsic alpha frequency (fIAF) calculated using the second EEG reading is <8.0 Hz or >13.0 Hz, then a third EEG recording is obtained and the previously described method of determining a final intrinsic alpha frequency of a subject (using a first EEG recording) is repeated using the third EEG recording in place of the first EEG recording. In some embodiments, if a standard deviation (SD) of the N epoch IAF values calculated using the third EEG reading ≥0.75 Hz, or if the final intrinsic alpha frequency (fIAF) calculated using the third EEG reading is <8.0 Hz or >13.0 Hz, then a fourth EEG recording is obtained and the previously described method of determining a final intrinsic alpha frequency of a subject (using a first EEG recording) is repeated using the fourth EEG recording in place of the first EEG recording. In some embodiments, if a standard deviation (SD) of the N epoch IAF values calculated using the fourth EEG reading ≥0.75 Hz, or if the final intrinsic alpha frequency (fIAF) calculated using the fourth EEG reading is <8.0 Hz or >13.0 Hz, then a fifth EEG recording is obtained and the previously described method of determining a final intrinsic alpha frequency of a subject (using a first EEG recording) is repeated using the fifth EEG recording in place of the first EEG recording. In some embodiments, if a standard deviation (SD) of the N epoch IAF values calculated using the fifth EEG reading ≥0.75 Hz, or if the final intrinsic alpha frequency (fIAF) calculated using the fifth EEG reading is <8.0 Hz or >13.0 Hz, then a sixth EEG recording is obtained and the previously described method of determining a final intrinsic alpha frequency of a subject (using a first EEG recording) is repeated using the sixth EEG recording in place of the first EEG recording. In some embodiments, if a standard deviation (SD) of the N epoch IAF values calculated using the sixth EEG reading ≥0.75 Hz, or if the final intrinsic alpha frequency (fIAF) calculated using the sixth EEG reading is <8.0 Hz or >13.0 Hz, then a seventh EEG recording is obtained and the previously described method of determining a final intrinsic alpha frequency of a subject (using a first EEG recording) is repeated using the seventh EEG recording in place of the first EEG recording. In some embodiments, if a standard deviation (SD) of the N epoch IAF values calculated using the seventh EEG reading ≥0.75 Hz, or if the final intrinsic alpha frequency (fIAF) calculated using the seventh EEG reading is <8.0 Hz or >13.0 Hz, then a eighth EEG recording is obtained and the previously described method of determining a final intrinsic alpha frequency of a subject (using a first EEG recording) is repeated using the eighth EEG recording in place of the first EEG recording. In some embodiments, if the final intrinsic alpha frequency (fIAF) calculated using the third EEG recording is <8.0 Hz or >13.0 Hz or if the standard deviation (SD) of the N epoch IAF values calculated using the third EEG reading ≥0.75 Hz, a range of fIAF intrinsic alpha frequencies (fIAFs) of the first EEG recording, the second EEG recording and the third EEG recording is calculated, wherein if the range is <2.0 Hz, then the mean value of the final intrinsic alpha frequencies (fIAFs) of the first EEG recording, the second EEG recording and the third EEG recording is determined to be the Valid intrinsic alpha frequency (vIAF). In still other embodiments, if the final intrinsic alpha frequency (fIAF) calculated using the eighth EEG recording is <8.0 Hz or >13.0 Hz or if the standard deviation (SD) of the N epoch IAF values calculated using the eighth EEG reading ≥0.75 Hz, a range of fIAF intrinsic alpha frequencies (fIAFs) of the at least three of the first EEG recording, the second EEG recording, the third EEG recording, the fourth EEG recording, the fifth EEG recording, the sixth EEG recording, the seventh EEG recording, the eighth EEG recording is calculated, wherein if the range is <2.0 Hz, then the mean value of the final intrinsic alpha frequencies (fIAFs) of at least three of the first EEG recording, the second EEG recording, the third EEG recording, the fourth EEG recording, the fifth EEG recording, the sixth EEG recording, the seventh EEG recording, the eighth EEG recording is determined to be the Valid intrinsic alpha frequency (vIAF).

In still other embodiments, if an $8^{th}$ EEG recording is performed and does not result in a Valid IAF, then the routine ends, and informs the user that a Valid IAF cannot be found.

Due to the previously noted "bursty" nature of Alpha waves in an EEG, it should be noted that the clinician should replace electrodes between each EEG and check electrode placement and electrode impedance. Also, the clinician must speak to the subject before each EEG, reminding the subject to relax, keep still, not move or open their eyes, clench their jaw, or shift around as these activities may exacerbate the problem. The flowchart in FIG. 1 provides an illustrative example of this discrimination routine.

Also as noted earlier, it has been shown that a magnetic field frequency within 1.0 Hz of the patient's IAF is required to obtain a benefit from NEST therapy. Therefore, the discrimination algorithm should be applied in order to find a valid IAF for each subject, and then exclude from the analysis those whose valid IAF is more than 1.0 Hz from the treatment frequency. In a trial, the baseline EEG can be used to determine the magnetic field frequency. However, weekly single-channel EEGs may also be recorded for each subject in a trial. A subject's natural IAF does not change significantly over time, and no evidence has been found from EEG evaluation that IAF values would change week to week during a treatment protocol.

Figure 2:
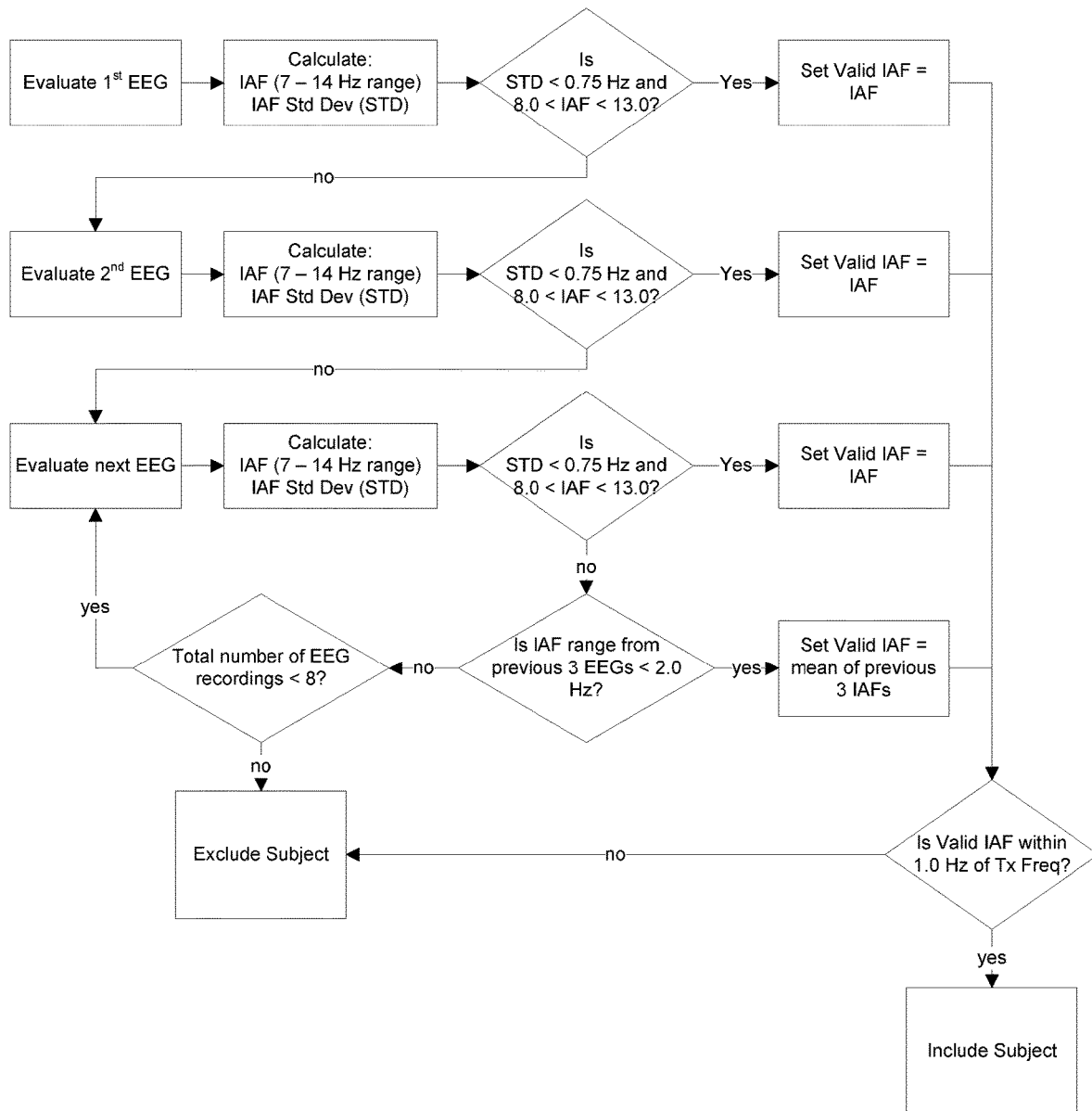
FIG. 2 is an illustrative flowchart of one aspect of the Inclusion/Exclusion decision tree for evaluation of the validity of the IAF.

The flowchart in FIG. 2 is a representative description of a process of using the EEG Discrimination algorithm from FIG. 1 as an inclusion/exclusion criterion for the clinical trial. In a trial, weekly EEGs are recorded for each subject. The magnetic field frequency is based on each subject's baseline EEG. The EEG Discrimination algorithm determines a valid IAF for the subject, using subsequent EEGs if necessary. If a valid IAF cannot be found, the subject is excluded. If a valid IAF is found which is not within 1.0 Hz of the treatment frequency (Tx Freq), then the subject is excluded as well. Otherwise, the subject is included in the analysis. The methodology that was used to compare the treatment frequency (Tx Freq), equal to the baseline EEG IAF value, with all recorded EEGs (up to 8) to determine if a subject had a valid baseline IAF, and includes the subject if the valid IAF is within 1.0 Hz of the Tx Freq. Final determination of a valid IAF resulted in a subject's inclusion or exclusion from eligibility for a clinical trial.

Provided herein is a method of determining a final intrinsic alpha frequency of a subject comprising applying an EEG discrimination routine comprising: obtaining a multi-channel EEG recording in a time domain; dividing the multi-channel EEG recording into a plurality of epochs, each epoch comprising a corresponding data segment from each channel, and averaging the data segments in each epoch together, wherein a total number of epochs is N; filtering the data segments of each epoch using a high-pass filter; converting each epoch into a frequency domain epoch (i); filtering each frequency domain epoch (i) using a smoothing filter; calculating an epoch intrinsic alpha frequency ($m_i$) of each frequency domain epoch (i); calculating a mean (M) intrinsic alpha frequency (IAF) of all intrinsic alpha frequencies ($m_{i-N}$), wherein $$M = \frac{1}{N}\sum_{i=1}^{N} m_i;$$

determining a farthest frequency domain epoch ($m_f$) from the mean M, wherein, i) if $|m_f - M| > 0.5$ Hz, removing the farthest frequency domain epoch ($m_f$), decrementing N, and returning to step g), or, ii) if $|m_f - M| \leq 0.5$ Hz, continuing to next step; setting a final intrinsic alpha frequency (fIAF) equal to M; and outputting the final intrinsic alpha frequency (fIAF) to a user or to a device.

In some embodiments, a channel intrinsic alpha frequency (cIAF) is determined for each channel in the frequency domain epoch (i) of a multi-channel EEG recording, and they are averaged together to generate the epoch intrinsic alpha frequency ($m_i$). In some embodiments, the epoch intrinsic alpha frequency ($m_i$) is generated by averaging channel intrinsic alpha frequencies generated from the channels meeting inclusion criteria and averaged together, wherein the inclusion criteria comprise: i) a greatest alpha power as compared to all other channels of the EEG recording; ii) a lowest variance as compared to all other channels of the EEG recording; or iii) a highest Q-factor as compared to all other channels of the EEG recording Provided herein is a method of determining a final intrinsic alpha frequency of a subject comprising applying an EEG discrimination routine comprising: obtaining a multi-channel EEG recording in a time domain; treating each channel separately, dividing each channel of multi-channel EEG recording into a plurality of epochs, each epoch comprising a segment data, from each channel, wherein a total number of epochs for each channel is N; filtering the data segments of each epoch, of each channel, using a high-pass filter; converting each epoch, of each channel, into a frequency domain epoch (i); filtering each frequency domain epoch (i), of each channel, using a smoothing filter; calculating an epoch intrinsic alpha frequency ($m_i$) of each frequency domain epoch (i) for each channel; calculating a mean (M) channel intrinsic alpha frequency (cIAF) of all intrinsic alpha frequencies ($m_{i-N}$) for each channel, wherein $$M = \frac{1}{N} \sum_{i=1}^{N} m_i;$$

determining a farthest frequency domain epoch ($m_f$) from the mean M for each channel, wherein, i) if $|m_f-M|>0.5$ Hz, removing the farthest frequency domain epoch ($m_f$), decrementing N, and returning to step g), or ii) if $|m_f-M|\leq 0.5$ Hz, continuing to next step; averaging the mean (M) channel intrinsic alpha frequency (cIAF) of all channels to determine a final intrinsic alpha frequency (fIAF); setting a final intrinsic alpha frequency (fIAF) equal to M for the entire multi-channel EEG recording; and outputting the final intrinsic alpha frequency (fIAF) to a user or to a device.

In some embodiments, a single channel intrinsic alpha frequency (cIAF) of the multi-channel EEG recording comprises; a frequency band between 8.0 Hz-13.0 Hz; a standard deviation (SD) below 0.75 Hz; the lowest (SD) of all the channel intrinsic alpha frequencies (cIAFs) of the multi-channel EEG recording; and the single channel intrinsic alpha frequency (cIAF) is selected as a representative intrinsic alpha frequency (IAF) for the multi-channel EEG recording.

In some embodiments, the intrinsic channel alpha frequencies (cIAFs) of all channels of the multi-channel EEG recording that are within a band between 8.0 Hz-13.0 Hz and have a standard deviation (SD) below 0.75 Hz; are averaged together to obtain a representative intrinsic alpha frequency (IAF) of the multi-channel time domain EEG recording.

In some embodiments, a multiple-channel time domain EEG recording may be used, wherein different options exist for determining the intrinsic alpha frequency (IAF). In one embodiment, each channel from the first multi-channel time domain EEG recording is treated separately and generates a channel intrinsic alpha frequency (cIAF) for each channel of the full multi-channel time domain EEG recording, wherein a number of channel intrinsic alpha frequencies (cIAFs) is equal to the number of channels from the first multi-channel time domain EEG recording. In some embodiments, all channel intrinsic alpha frequencies (cIAFs) from the first multi-channel time domain EEG recording are averaged together to obtain a representative intrinsic alpha frequency (IAF) of the multi-channel time domain EEG recording. In some embodiments a single channel alpha frequency (cIAF) of the first multi-channel time domain EEG recording is within a band between 8.0 Hz-13.0 Hz; has a standard deviation (SD) below 0.75 Hz; has the lowest (SD) of all the channel intrinsic alpha frequencies (cIAFs) of the multi-channel time domain EEG recording; and is selected as a representative intrinsic alpha frequency (IAF) of the multi-channel time domain EEG recording. Still further, the channel intrinsic alpha frequency (cIAF) of all channels of the first multi-channel time domain EEG recording that are within a band between 8.0 Hz-13.0 Hz; and have a standard deviation (SD) below 0.75 Hz; are averaged together to obtain a representative intrinsic alpha frequency (IAF) of the multi-channel time domain EEG recording.

Provided herein is a method of determining a valid intrinsic frequency (vIF) of an EEG band of a subject comprising: applying an EEG discrimination routine comprising: obtaining a first EEG recording in a time domain; dividing the first EEG recording into a plurality of epochs, wherein a total number of epochs is N; filtering the data using a high-pass filter (to reduce the influence of heartbeat and low frequency noise); converting each epoch into a frequency domain epoch (i); filtering each frequency domain epoch (i) using a smoothing filter; calculating an epoch intrinsic frequency ($m_i$) in an EEG band of each frequency domain epoch (i); calculating a mean (M) intrinsic frequency (IF) in the EEG band of all epoch intrinsic frequencies ($m_{i-N}$), wherein $$M = \frac{1}{N} \sum_{i=1}^{N} m_i;$$

determining the farthest frequency domain epoch ($m_f$) from the mean, wherein if $|m_f-M|>0.5$ Hz, removing the farthest frequency domain epoch ($m_f$) decrementing N, and returning to the step for calculating a mean (M) intrinsic frequency (IF) in the band of all epoch intrinsic frequencies, or if $|m_f-M|\leq 0.5$ Hz, then; continue to the next step for setting a final intrinsic frequency (fIF) equal to M; and outputting the final intrinsic frequency (fIF) in the EEG band equal to M; and outputting the final intrinsic frequency (fIF) in the EEG band to a user or device. In some embodiments, wherein determining a farthest frequency domain epoch ($m_f$) from the mean M comprises determining an index (I) of frequency domain epoch that is farthest from the mean (M), wherein I=Index(max$_i|m_i-M|$). In some embodiments, the EEG band comprises: an Alpha band; a Theta band; a Beta band; a Gamma band; and a Delta band. In some embodiments, the EEG recording length is 128 seconds. In some embodiments, the EEG recording is a single-channel recording. In some embodiments, the EEG recording is a multi-channel recording. In some embodiments the EEG is a multi-channel recording, wherein a channel intrinsic frequency (cIF) estimate may be made for each channel in an epoch and averaged together, or wherein each channel is treated separately, generating a final intrinsic frequency (fIF) estimate for each channel for the full EEG recording, and wherein final intrinsic frequency estimates from each channel, as determined by step h), are averaged together to generate a final intrinsic frequency (fIF). In some embodiments, a channel of the EEG comprises 16 epochs. In some embodiments, the calculated epoch intrinsic frequency ($m_i$) of the EEG comprises a range that is at least: ±0.5 Hz outside the range of the EEG band; ±1.0 Hz outside the range of the EEG band; ±1.5 Hz outside the range of the EEG band; and ±2.0 Hz outside the range of the EEG band. In some embodiments, the EEG recording comprises a sample rate of 128 samples/sec. In some embodiments, the high-pass filter uses a 4$^{th}$ order Butterworth IIR filter with the 3 dB cutoff set to 5.0 Hz. In some embodiments, the epoch intrinsic frequency of each epoch ($m_i$) is determined using a Fast Fourier Transform (FFT). In some embodiments, the Fast Fourier Transform (FFT) uses a resolution of 1024 points, which results in a 0.125 Hz resolution per bin from 0 Hz to 64 Hz. In some embodiments, the Fast Fourier Transform (FFT) is smoothed with an averaging filter that averages 5 points±2 from the target. In some embodiments, if the standard deviation (SD) of the N epoch IF value is ≥0.75 Hz, a second EEG recording is obtained and the previously described method of determining a valid intrinsic frequency (vIF) of an EEG band of a subject (using a first EEG recording) is repeated using the second EEG recording in place of the first recording. In some embodiments, if the standard deviation (SD) of the N epoch IF values calculated using the second EEG recording is ≥0.75 Hz, a third EEG recording is obtained and the previously described method of determining a valid intrinsic frequency (vIF) of an EEG band of a subject (using a first EEG recording) is repeated using the third EEG recording in place of the first recording. In some embodiments, if the standard deviation (SD) of the N epoch IF values calculated using the third EEG recording is ≥0.75 Hz, a fourth EEG recording is obtained and the previously described method of determining a valid intrinsic frequency (vIF) of an EEG band of a subject (using a first EEG recording) is repeated using the fourth EEG recording in place of the first recording. In some embodiments, if the standard deviation (SD) of the N epoch IF values calculated using the fourth EEG recording is ≥0.75 Hz, a fifth EEG recording is obtained and the previously described method of determining a valid intrinsic frequency (vIF) of an EEG band of a subject (using a first EEG recording) is repeated using the fifth EEG recording in place of the first recording. In some embodiments, if the standard deviation (SD) of the N epoch IF values calculated using the fifth EEG recording is ≥0.75 Hz, a sixth EEG recording is obtained and the previously described method of determining a valid intrinsic frequency (vIF) of an EEG band of a subject (using a first EEG recording) is repeated using the sixth EEG recording in place of the first recording. In some embodiments, if the standard deviation (SD) of the N epoch IF values calculated using the sixth EEG recording is ≥0.75 Hz, a seventh EEG recording is obtained and the previously described method of determining a valid intrinsic frequency (vIF) of an EEG band of a subject (using a first EEG recording) is repeated using the seventh EEG recording in place of the first recording. In some embodiments, if the standard deviation (SD) of the N epoch IF values calculated using the seventh EEG recording is ≥0.75 Hz, an eighth EEG recording is obtained and the previously described method of determining a valid intrinsic frequency (vIF) of an EEG band of a subject (using a first EEG recording) is repeated using the eighth EEG recording in place of the first recording. In still other embodiments, if the eighth standard deviation (SD) of the N epoch IF values is ≥0.75 Hz obtained using the eighth EEG recording, a range of final intrinsic frequencies (fIFs) of at least three of the first EEG recording, the second EEG recording, the third EEG recording, the fourth EEG recording, the fifth EEG recording, the sixth EEG recording, the seventh EEG recording, and the eighth EEG recording is calculated, wherein if the range is <2.0 Hz, then the mean value of the final intrinsic frequencies (fIFs) of at least three of the first EEG recording, the second EEG recording, the third EEG recording, the fourth EEG recording, the fifth EEG recording, the sixth EEG recording, the seventh EEG recording, and the eighth EEG recording is determined to be the Valid intrinsic frequency (vIF). In some embodiments, if a third standard deviation (SD) of the N epoch IF values ≥0.75 Hz obtained using the third EEG recording, a range of final intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). In some embodiments of the method of determining a valid intrinsic frequency (vIF) of an EEG band of a subject, if the final intrinsic frequency (fIF) of the EEG recording is > a predetermined amount outside the EEG band, a second EEG recording is obtained and the method of determining a valid intrinsic frequency (vIF) of an EEG band of a subject is repeated using the second EEG recording in place of the first EEG recording. In some embodiments, the predetermined amount is: ±0.5 Hz; ±1.0 Hz; ±1.5 Hz; or ±2.0 Hz. In some embodiments, if the final intrinsic frequency (fIF) of the EEG recording obtained using the second EEG recording is > the predetermined amount outside the EEG band, a third EEG recording is obtained and the previously described method of determining a valid intrinsic frequency (vIF) of an EEG band of a subject (using a first EEG recording) is repeated using the third EEG recording in place of the first recording. In some embodiments, if the final intrinsic frequency (fIF) of the EEG recording obtained using the third EEG recording is > the predetermined amount outside the EEG band, a fourth EEG recording is obtained and the previously described method of determining a valid intrinsic frequency (vIF) of an EEG band of a subject (using a first EEG recording) is repeated using the fourth EEG recording in place of the first recording. In some embodiments, if the final intrinsic frequency (fIF) of the EEG recording obtained using the fourth EEG recording is > the predetermined amount outside the EEG band, a fifth EEG recording is obtained and the previously described method of determining a valid intrinsic frequency (vIF) of an EEG band of a subject (using a first EEG recording) is repeated using the fifth EEG recording in place of the first recording. In some embodiments, if the final intrinsic frequency (fIF) of the EEG recording obtained using the fifth EEG recording is > the predetermined amount outside the EEG band, a sixth EEG recording is obtained and the previously described method of determining a valid intrinsic frequency (vIF) of an EEG band of a subject (using a first EEG recording) is repeated using the sixth EEG recording in place of the first recording. In some embodiments, if the final intrinsic frequency (fIF) of the EEG recording obtained using the sixth EEG recording is > the predetermined amount outside the EEG band, a seventh EEG recording is obtained and the previously described method of determining a valid intrinsic frequency (vIF) of an EEG band of a subject (using a first EEG recording) is repeated using the seventh EEG recording in place of the first recording. In some embodiments, if the final intrinsic frequency (fIF) of the EEG recording obtained using the seventh EEG recording is > the predetermined amount outside the EEG band, an eighth EEG recording is obtained and the previously described method of determining a valid intrinsic frequency (vIF) of an EEG band of a subject (using a first EEG recording) is repeated using the eighth EEG recording in place of the first recording. In some embodiments, if the final intrinsic frequency (fIF) calculated using the third EEG recording is > the predetermined amount outside the EEG band, a range of final intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). In some embodiments, if the final intrinsic frequency (fIF) calculated using the third EEG recording is > the predetermined amount outside the EEG band, a range of final intrinsic frequencies (fIFs) of three or more of the first EEG recording, the second EEG recording, the third EEG recording, the fourth EEG recording, the fifth EEG recording, the sixth EEG recording, the seventh EEG recording, and the eighth EEG recording is calculated, wherein if the range is <2.0 Hz, then the mean value of the final intrinsic frequencies (fIFs) of the three or more of the first EEG recording, the second EEG recording, the third EEG recording, the fourth EEG recording, the fifth EEG recording, the sixth EEG recording, the seventh EEG recording, and the eighth EEG recording is determined to be the Valid intrinsic frequency (vIF).

In some embodiments of the method of determining a valid intrinsic frequency (vIF) of an EEG band of a subject, if a standard deviation (SD) of the N epoch IF values ≥0.75 Hz, or if the final intrinsic frequency (fIF) is > a predetermined amount outside the EEG band, wherein the predetermined amount is ±0.5 Hz, ±1.0 Hz, ±1.5 Hz, or ±2.0 Hz; then a second EEG recording is obtained and the previously described method of determining a valid intrinsic frequency (vIF) of an EEG band of a subject (using a first EEG recording) is repeated using the second EEG recording in place of the first EEG recording. In some embodiments, if a standard deviation (SD) of the N epoch IF values calculated using the second EEG reading ≥0.75 Hz, or if the final intrinsic frequency (fIF) calculated using the second EEG reading is > the predetermined amount outside the EEG band, then a third EEG recording is obtained and the previously described method of determining a valid intrinsic frequency (vIF) of an EEG band of a subject (using a first EEG recording) is repeated using the third EEG recording in place of the first EEG recording. In some embodiments, if a standard deviation (SD) of the N epoch IF values calculated using the third EEG reading ≥0.75 Hz, or if the final intrinsic frequency (fIF) calculated using the third EEG reading is > the predetermined amount outside the EEG band, then a fourth EEG recording is obtained and the previously described method of determining a valid intrinsic frequency (vIF) of an EEG band of a subject (using a first EEG recording) is repeated using the fourth EEG recording in place of the first EEG recording. In some embodiments, if a standard deviation (SD) of the N epoch IF values calculated using the fourth EEG reading ≥0.75 Hz, or if the final intrinsic frequency (fIF) calculated using the fourth EEG reading is > the predetermined amount outside the EEG band, then a fifth EEG recording is obtained and the previously described method of determining a valid intrinsic frequency (vIF) of an EEG band of a subject (using a first EEG recording) is repeated using the fifth EEG recording in place of the first EEG recording. In some embodiments, if a standard deviation (SD) of the N epoch IF values calculated using the fifth EEG reading ≥0.75 Hz, or if the final intrinsic frequency (fIF) calculated using the fifth EEG reading is > the predetermined amount outside the EEG band, then a sixth EEG recording is obtained and the method of claim 35 is repeated using the sixth EEG recording in place of the first EEG recording. In some embodiments, if a standard deviation (SD) of the N epoch IF values calculated using the sixth EEG reading ≥0.75 Hz, or if the final intrinsic frequency (fIF) calculated using the sixth EEG reading is > the predetermined amount outside the EEG band, then a seventh EEG recording is obtained and the previously described method of determining a valid intrinsic frequency (vIF) of an EEG band of a subject (using a first EEG recording) is repeated using the seventh EEG recording in place of the first EEG recording. In some embodiments, if a standard deviation (SD) of the N epoch IF values calculated using the seventh EEG reading ≥0.75 Hz, or if the final intrinsic frequency (fIF) calculated using the seventh EEG reading is > the predetermined amount outside the EEG band, then a eighth EEG recording is obtained and the previously described method of determining a valid intrinsic frequency (vIF) of an EEG band of a subject (using a first EEG recording) is repeated using the eighth EEG recording in place of the first EEG recording. In still further embodiments, if the final intrinsic frequency (fIF) calculated using the third EEG recording is > the predetermined amount outside the EEG band, or if the standard deviation (SD) of the N epoch IF values calculated using the third EEG reading ≥0.75 Hz, a range of final intrinsic frequencies (fIFs) of the first EEG recording, the second EEG recording and the third EEG recording is calculated, wherein if the range is <2.0 Hz, then the mean value of the final intrinsic frequencies (fIFs) of the first EEG recording, the second EEG recording and the third EEG recording is determined to be the Valid intrinsic frequency (vIF). Further still, in some embodiments, if the final intrinsic frequency (fIF) calculated using the eighth EEG recording is > the predetermined amount outside the EEG band or if the standard deviation (SD) of the N epoch IF values calculated using the eighth EEG reading ≥0.75 Hz, a range of final intrinsic frequencies (fIFs) of the at least three of the first EEG recording, the second EEG recording, the third EEG recording, the fourth EEG recording, the fifth EEG recording, the sixth EEG recording, the seventh EEG recording, the eighth EEG recording is calculated, wherein if the range is <2.0 Hz, then the mean value of the final intrinsic frequencies (fIFs) of the at least three of the first EEG recording, the second EEG recording, the third EEG recording, the fourth EEG recording, the fifth EEG recording, the sixth EEG recording, the seventh EEG recording, the eighth EEG recording is determined to be the Valid intrinsic frequency (vIF).

In some embodiments of the method of determining a valid intrinsic frequency (vIF) of an EEG band of a subject, if the final intrinsic frequency (fIF) is within the EEG band and the standard deviation (SD) of the N epoch IF value is <0.75 Hz, the final intrinsic frequency (fIF) is determined to be a valid intrinsic frequency (vIF). In some embodiments, a channel intrinsic frequency (cIF) is determined for each channel in the frequency domain epoch (i), and they are averaged to generate the epoch intrinsic frequency ($m_i$). In some embodiments, an epoch intrinsic frequency ($m_i$) is generated by averaging channel intrinsic frequencies (cIFs) generated from the channels meeting inclusion criteria and averaged together, wherein the inclusion criteria comprise: a greatest power in the EEG band as compared to all other channels of the EEG recording; a lowest variance as compared to all other channels of the EEG recording; or a highest Q-factor as compared to all other channels of the EEG recording.

Further still, in some embodiments, each channel from a multi-channel time domain EEG recording is treated separately and generates a channel intrinsic frequency (cIF) for each channel of the full multi-channel time domain EEG recording, wherein a number of channel intrinsic frequencies (cIFs) is equal to the number of channels from the multi-channel time domain EEG recording. In other embodiments, all channel intrinsic frequencies (cIFs) from a multi-channel time domain EEG recording are averaged together to obtain a representative intrinsic frequency (IF) of the multi-channel time domain EEG recording. In some embodiments, the channel intrinsic frequency (cIF) of a single channel of a multi-channel time domain EEG recording comprises: a standard deviation (SD) below 0.75 Hz; the lowest (SD) of all the channel intrinsic frequencies (cIFs) of the multi-channel time domain EEG recording; and is selected as a representative intrinsic frequency (IF) of the multi-channel time domain EEG recording. In still other embodiments, all channel intrinsic frequencies (cIFs) of channels of a multi-channel time domain EEG recording that have a standard deviation (SD) below 0.75 Hz; are averaged together to obtain a representative intrinsic frequency (IF) of the multi-channel time domain EEG recording.

Use of the Invention

To use the invention, an EEG is recorded from the patient. The algorithm will generate an IAF estimate for the patient and label it as either "valid" or "suspect", depending on whether or not it is in band and stable. If the IAF is valid, then the procedure ends. If the IAF is suspect, then another EEG may need to be recorded. This process continues until either a valid IAF is generated or 8 EEG recordings have been completed. If the subject reaches 8 EEGs without a valid IAF, the subject is informed that he or she does not have an EEG that contains a detectable alpha frequency.

A single-channel EEG or multiple-channel EEG may be used. For a multiple-channel EEG, different options exist for determining the IAF of an EEG recording.

In one aspect, an IAF estimate may be made for each channel in an epoch and then averaged together. IAF estimates from all channels for a single epoch could be averaged together.

Alternately, IAF estimates only from channels whose EEGs meet a specific criteria could be averaged, such as: Greatest alpha power; Lowest variance; or Highest Q factor.

In one aspect, each channel is treated separately, generating its own IAF estimate for the full recording. In the end, a number of IAF estimates exist equal to the number of channels. Afterward, valid IAF estimates from the channels can be averaged together for a final IAF estimate for the EEG recording.

Alternately, the channel that is in band with the lowest standard deviation could be used as the representative channel for the EEG recording.

Alternately, all channels which are in band with a standard deviation below 0.75 Hz could be averaged together to get an IAF estimate for the full recording.

In a preferred aspect, the intrinsic frequency of the Alpha band is calculated. Alternately, the intrinsic frequency of other EEG bands could be calculated. These include: the Theta band; the Beta band; the Gamma band; and the Delta band.

In the part of the routine to find peak IAF of a single epoch, the window to find the peak is 1.0 Hz outside the EEG band of interest. The decision of the window width may be different depending on the EEG band, the patient, or the therapy being provided. In one aspect, the window is 0.5 Hz outside the EEG band of interest. In one aspect, the window is 1.5 Hz outside the EEG band of interest. In one aspect, the window is 2.0 Hz outside the EEG band of interest.

Figure 3:
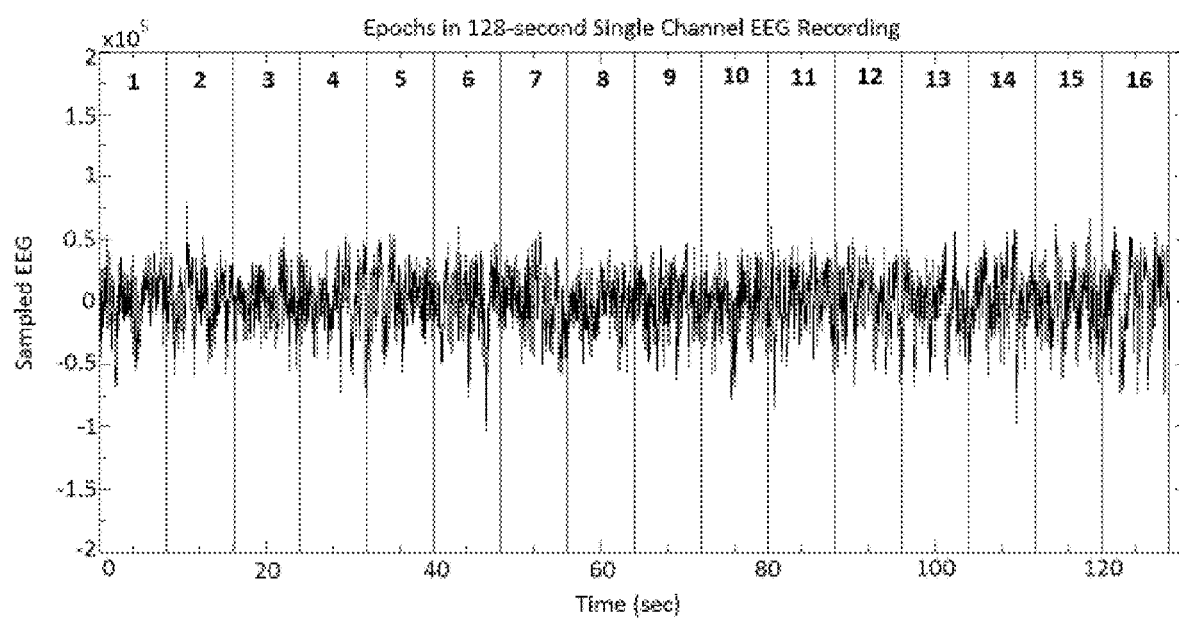
FIG. 3 is an illustrative example of a 128 second EEG recording divided into 16 Epochs.
Figure 4:
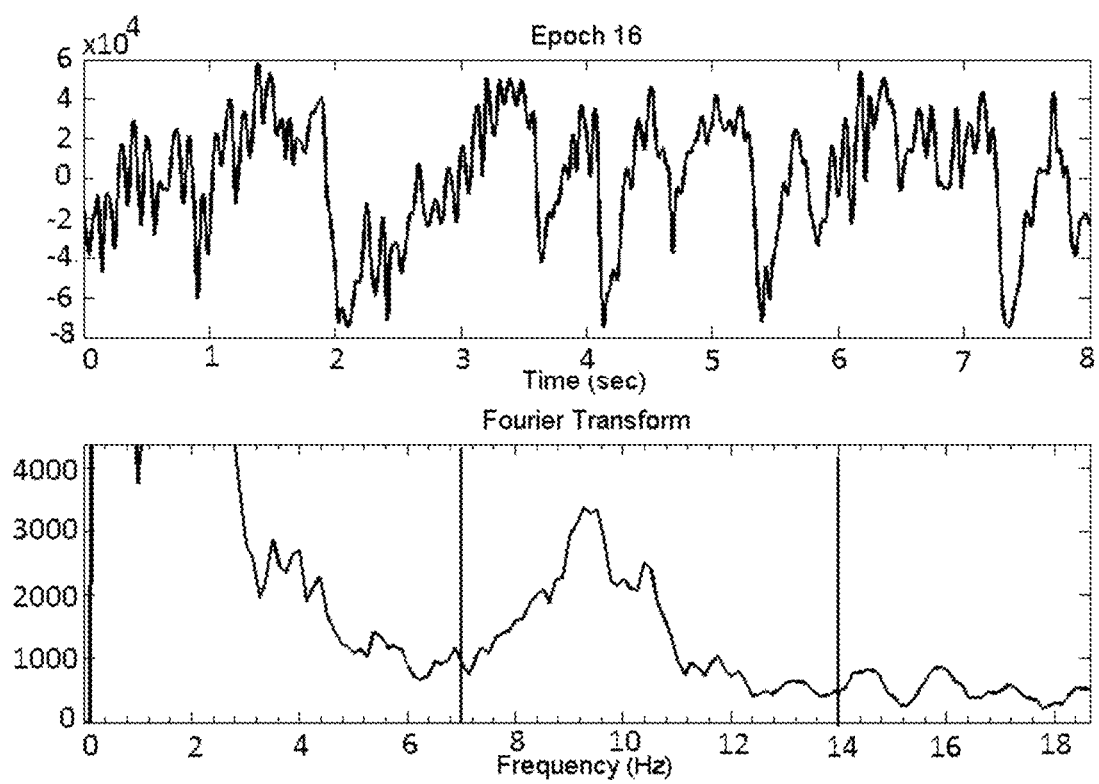
FIG. 4 is an illustrative example of a single epoch plot, showing the filtered EEG (top plot), along with the FFT of the epoch (bottom plot), focusing on the frequency between 0-20 Hz. The window size of 7-14 Hz is shown by 2 vertical lines.

There were several variables that can be chosen for the algorithm, which may change based on the EEG band, the patient, or the therapy. Some of these include: EEG recording length (Preferred: 128 seconds); Sample rate (Preferred: 128 Hz); Filtering settings (filter type, order, cutoff frequency), wherein a preferred filtering includes: Butterworth, $4^{th}$ order, 5.0 Hz.; FFT resolution (Preferred: 1024 point), (with an example of the output illustrated by FIG. 4); Averaging filter settings (Preferred: +/−2 samples); Number of epochs, (Preferred=16, as illustrated in FIG. 3); Number of channels (Preferred: 1); Distance from the mean threshold to remove epochs (Preferred: 0.5 Hz); Standard deviation threshold to label an IAF as suspect (Preferred: 0.75 Hz); the number of EEG recordings before the additional option to average a number of previous EEGs in finding a valid IAF (Preferred: 3); the number of EEG recordings averaged to find a valid IAF (Preferred: 3); and, the number of EEG recordings without a valid IAF before the algorithm informs the user that none can be found (Preferred: 8).

Validation of the Discrimination Algorithm—Example 1

The EEG recordings from a clinical trial database formed the test set for a validation of the algorithm (See ClinicalTrials.gov registration #NCT01370733). The validation was performed to ensure that at least 90% of subjects in the test set were found to have a recalculated IAF estimate that is within 1.0 Hz away from the treatment frequency used in a clinical trial. In addition, an expert qualitative analysis was performed on those subjects whose recalculated IAF estimates were more than 1.0 Hz away from the baseline estimate.

229 subjects were evaluated out of the total of 231. Two subjects had no EEGs available due to an error made when downloading the EEGs. Five of the subjects did not have a stable EEG to get a valid IAF.

Of the 229 subjects, 22 either had a recalculated IAF that was greater than 1.0 Hz from the baseline IAF or were unable to determine a valid IAF. It was noted that these were the same subjects that were previously excluded from the "per protocol" analysis of a clinical trial. In the majority of the remaining subjects, the new algorithm produced an IAF value that was exactly the same as original treatment frequency used in the clinical study. Result: (22 inaccurate IAFs)/(229 subjects)=9.6%, which is less than 10.0%. PASS.

Provided herein is a device comprising a computer-implemented system configured to discriminate a valid intrinsic alpha frequency of at least one time domain EEG recording of a subject comprising a software module with a routine configured to: evaluate a first time domain EEG recording of a subject; determine if the time domain EEG recording has a stable intrinsic alpha frequency ($m_i$) throughout a plurality of epochs wherein a valid intrinsic alpha frequency comprises; a standard deviation between the epochs is <0.75 Hz, and a mean (M) of epoch intrinsic alpha frequencies ($m_i$) between 8.0 Hz to 13.0 Hz; set a final intrinsic alpha frequency (fIAF) equal to M; and output the final intrinsic alpha frequency (fIAF) to the device; or, label the first time domain EEG recording suspect; and continue to sequentially evaluate a plurality of subsequent time domain EEG recordings until a valid intrinsic alpha frequency can be obtained from a subsequent time domain EEG recording. In some embodiments of the computer implemented system, a total number of time domain EEG recordings is eight. In some embodiments of the computer implemented system, if the software module routine cannot obtain a valid intrinsic alpha frequency within the first time domain EEG recording, a second time domain EEG recording or a third time domain EEG recording, a range of epoch intrinsic alpha frequencies ($m_i$) of the first time domain EEG recording, the second time domain EEG recording and the third time domain EEG recording is calculated, wherein if the range is <2.0 Hz, the mean (M) of the first time domain EEG recording, the second time domain EEG recording and the third time domain EEG recording is calculated and is set equal to the final intrinsic alpha frequency (fIAF). In some embodiments of the computer implemented system, if the software module routine cannot obtain a valid intrinsic alpha frequency within eight time domain EEG recordings, the software module routine ends and outputs a message to a user that a valid intrinsic alpha frequency cannot be found. In some embodiments, the device comprises a Neuro-EEG Synchronization Therapy (NEST) device. In some embodiments, the device is configured to deliver low amplitude stimulation at an intrinsic alpha frequency that is the same as a patient's intrinsic alpha frequency.

Provided herein is a method of quantitatively analyzing EEG recordings to obtain a valid Intrinsic Alpha Frequency of a subject using a Neuro-EEG Synchronization Therapy (NEST) device comprising: obtaining a single 128-second time domain EEG recording; dividing the 128-second EEG recording into sixteen eight-second epochs; converting each epoch into a frequency domain epoch (i); calculating an epoch intrinsic alpha frequency ($m_i$) for each frequency domain epoch (i); successively eliminating the epoch intrinsic alpha frequencies ($m_i$) that are farthest from a mean, until the remaining epoch intrinsic alpha frequencies ($m_i$) are all within 0.5 Hz of the mean; and outputting a final intrinsic alpha frequency (fIAF) for the EEG recording that is equal to the mean value of the remaining epochs' epoch intrinsic alpha frequencies. In some embodiments, the final intrinsic alpha frequency (fIAF) is determined to be valid if the standard deviation of the epoch intrinsic alpha frequencies ($m_i$) from the epochs is <0.75 Hz and the final intrinsic alpha frequency (fIAF) is within the band of 8.0-13.0 Hz. In some embodiments, the final intrinsic alpha frequency (fIAF) is determined to be suspect if a standard deviation of the epoch intrinsic alpha frequencies ($m_i$) from the epochs is ≥0.75 Hz or the final intrinsic alpha frequency (fIAF) is outside the band of 8.0-13.0 Hz, and wherein a second EEG is recorded is obtained to determine if a valid intrinsic alpha frequency (vIAF) can be determined as defined previously, by replacing the single 128-second time domain EEG recording with the second EEG recording. In some embodiments, the final intrinsic alpha frequency (fIAF) using the second EEG recording is determined to be suspect if a standard deviation of the epoch intrinsic alpha frequencies ($m_i$) from the epochs is ≥0.75 Hz or the final intrinsic alpha frequency (fIAF) is outside the band of 8.0-13.0 Hz, and wherein a third EEG recording is obtained to determine if the valid intrinsic alpha frequency (vIAF) can be determined as defined previously, by replacing the single 128-second time domain EEG recording with the third EEG recording. In some embodiments, if the valid intrinsic alpha frequency (vIAF) cannot be obtained using the third EEG recording, a range of the final intrinsic alpha frequency (fIAF) values of the three previous EEG recordings is calculated, and if the range of the previous three final intrinsic alpha frequency (fIAF) values is <2.0 Hz, then the valid Intrinsic Alpha Frequency (vIAF) is set to the mean of the three previous final Intrinsic Alpha Frequencies (fIAFs).

In some embodiments of the method of determining a final intrinsic alpha frequency of a subject, wherein determining the farthest frequency domain epoch ($m_f$) from the mean M comprises calculating an index (I) of the frequency domain epoch that is farthest from the mean (M), wherein I=Index($max_i|m_i-M|$). In some embodiments of the method of determining a valid intrinsic frequency of an EEG band of a subject, wherein determining the farthest frequency domain epoch ($m_f$) from the mean M comprises calculating an index (I) of the frequency domain epoch that is farthest from the mean (M), wherein I=Index($max_i|m_i-M|$).

In some embodiments, up to eight EEG recordings are performed in an attempt to obtain a valid intrinsic alpha frequency (vIAF) if a valid Intrinsic Alpha Frequency is not obtained as previously defined. In some embodiments, the quantitative analysis ends if a valid Intrinsic Alpha Frequency cannot be determined after eight recordings.

Digital Processing Device

In some embodiments, the platforms, systems, media, and methods described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, vehicles, and wearable computing devices. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art. Those of skill in the art will recognize wearable computing devices suitable to work with the platforms, systems, media, and methods described herein comprise a smart watch, smart glasses (e.g., Google Glass®, Microsoft HoloLens®), clothing comprising computing devices, and any other computing device that can be attached to or worn by a person and/or animal.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In various embodiments, the input device is a device capable of recognizing one or more physical gestures and/or motions. In further embodiments, the input device is a Microsoft Kinect®, Leap Motion®, or the like. In still further embodiments, the input device is a combination of devices such as those disclosed herein.

Server Configuration

In some embodiments, a suitable server configuration includes about 1, about 2, about 3, about 4, about 5, about 6, about 7, about 8, about 9, about 10, about 20, about 30, about 40, about 50, about 60, about 70, about 80, about 90, about 100, about 200, about 500, about 1000, more than about 1000 servers, one or more server farms, and cloud-based server resource allocation systems. In some embodiments, the servers are co-located. In some embodiments, the servers are located in different geographical locations. In some embodiments the servers are housed in the same rack. In some embodiments, the servers are housed in multiple racks. In some embodiments, the multiple racks are in the same geographic region. In some embodiments the racks are in different geographic regions. In some embodiments, the server is or a plurality of servers employ a software framework such as Hadoop, Google MapReduce, HBase, and/or Hive, for storage and large-scale processing of data-sets on clusters of hardware.

Non-transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. As a non-limiting example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of item, buyer, and seller information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Input and Output Devices

In some embodiments, the platforms, systems, media, and methods disclosed herein include one or more input devices or output devices, or use of the same. In view of the disclosure provided herein, those of skill in the art will recognize that many devices are suitable for inputting and/or outputting information EEG data and/or frequency information of a subject. In various embodiments, suitable devices includes: a digital display, a keyboard, a touch-screen, computer readable medium, a EEG sensor, a EEG recording device, an auxiliary connection, a USB connection, an electrode, an interactive interface, a user interface, a mouse, a microphone, a joy stick, light pen, a scanner, a graphic tablet, a magnetic ink card reader(micr), optical character reader(ocr), a computer readable medium reader, optical mark reader(omr), or the like.

Validation of the Discrimination Algorithm—Example 2

30 subjects (14 male, 16 female, 33.8±11.5 yrs old) participated in the validation study (See ClinicalTrials.gov registration #NCT01370733). The subjects had a varied ethnic mix (16 white, 5 Asian, 4 Hispanic, 1 Pacific Islander, and 4 mixed races). 15 of the subjects underwent EEG recording in the morning, and 15 in the afternoon. Each subject underwent three different phases: Phase 1: eyes closed, relaxed; Phase 2: eyes open; and Phase 3: eyes closed, with muscle artifact.

Three disposable patch Ag—AgCl snap-type electrodes are affixed to the subject's head, one in the center of the forehead (FpZ) approximately 1" (two fingers) above the nasal bridge between the eyebrows; one on the subject's forehead right of center (Fp1); and one (OZ) approximately 1" (two fingers) above the protuberance of the occipital bone (inion). EEG recording is done automatically at the push of the START button on the NeoSync NEST Device. Preferred embodiments of the NeoSync NEST Device are described in the related U.S. patent application Ser. Nos. 12/237,319, 12/237,328, and 12/237,304, 12/850,547, 12/944,591, 13/681,964, all of the above identified applications previously mentioned are incorporated herein by reference.

In this validation study, the test device is not used to deliver therapy to subject but instead to acquire and interpret EEG signal. The hardware and/or software module specific to acquiring and interpreting an EEG signal is internal to the NeoSync NEST Device and is the component evaluated during this study.

IAF stands for Individual Alpha Frequency; sTMS stands for synchronized Transcranial Magnetic Stimulation; NVC, MJA, DJB, SC are initials of technicians performing the EEG recording; CVS is the initial for an outside consultant who performed an independent analysis of the EEG recordings.

There were 4 technicians who recorded EEGs. Two of the technicians (NVC and MJA) were experienced, having performed numerous EEG recordings during the NND-3001 NEST clinical trial. The other two technicians (DJB and SC) were inexperienced, having never recorded an EEG with the NEST device or otherwise. All four technicians underwent training on electrode application, device connectivity and use, and EEG acquisition as part of the study.

To determine the effect of technician experience, we evaluated the average number of recordings to obtain a valid EEG during Phase 1. The experienced technicians recorded EEGs for 14 subjects, with an average of 2.57±2.44 recordings for a valid IAF. The inexperienced technicians recorded EEGs for 16 subjects, with an average of 2.31±2.47 recordings. Using a 2-tailed t-test, the p value of the number of recording to obtain a valid IAF equals 0.77 and thus, there is no statistical significance between the experienced and inexperienced technicians. Therefore, experience level of the technician is not considered a factor in obtaining a valid IAF.

Among all of the 30 test subjects, average number of EEG recording attempts to obtain a valid IAF during Phase 1 was 1.57, and number of subjects excluded, due to 8 invalid IAF recordings during Phase was 4 out of 30, which is 13%. IAF consistency between Phase 1 and Phase 2, Phase 1 and Phase 3 was tested. 0.0% of the test subject had more than 1.0 Hz difference.

IAF estimation was also compared to blinded independent calculation of IAF. The average difference identified across all subjects was 0.175 Hz. Only 1 of the subject, 3.33% of the total number of subjects, had more than 1.0 Hz difference when compared to blinded independent calculation of IAF.

Average difference between IAF from first recording segment Phase 1 and the final valid IAF was 0.141 Hz. Only 1 subject, 3.33% of the total number of subjects, had more than 1.0 Hz difference between the IAF measured from the first recording segment and the final valid IAF.

The average absolute difference in IAFs between Phase 1 and Phase 2 or 3 was 0.33 Hz, which indicates that the measurement is consistent and not greatly affected by noise artifact. There were no subjects that had a difference in IAFs between phases that is greater than 1.0 Hz. There were 5 subjects with absolute difference in IAFs of greater than 0.5 Hz between Phase 1 and Phase 2/3. The EEGs of these individuals were generally very noisy or had certain characteristics, such as a double-hump, which led to the difference. The highest absolute difference was 0.865 Hz. Noise artifact, obtained from jaw clenching, eye rolling behind closed lids, frowning, etc. did not appear to be a factor in obtaining a valid IAF. Based on these results, the discrimination routine has been shown to be very effective at finding a consistent, stable, valid IAF and rejecting noisy EEGs.

Interestingly, 14/30 subjects obtained a valid IAF during Phase 2 (eyes open). Although this is not the preferred method of recording an EEG, it is encouraging that even if subjects are not fully compliant during EEG recording, a valid IAF may still be found.

One of the technicians, MJA, recorded a disproportionally large number of noisy EEGs where a valid IAF was unable to be obtained. In order to better understand this relationship, a follow-up meeting was scheduled where the technician repeated the recording procedure (skin prep, electrode placement, etc.) on an additional subject. Issues identified in the recording technique were that an alcohol wipe was not used before applying the abrasive gel, and the rear electrode was placed approximately 1" too low, situated almost directly over the inion bone. Neither of these resulted in any excessive noise artifact in an analysis of the EEG recording.

The EEG data from Phase 1 was analyzed independently by CVS, who is experienced in EEG analysis and algorithm development. His estimates differed on average −0.076 Hz from the IAF produced by the EEG discrimination algorithm. The average absolute difference was 0.175 Hz. This independent analysis confirms that the EEG system generates repeatable, reliable IAF estimates that correlate well with independent qualitative analysis.

There were specific subjects in the study who had EEGs that were very noisy or had unique characteristics (e.g., double-hump, out-of-band peaks), which gave the algorithm problems in finding a valid IAF.

Figure 5:
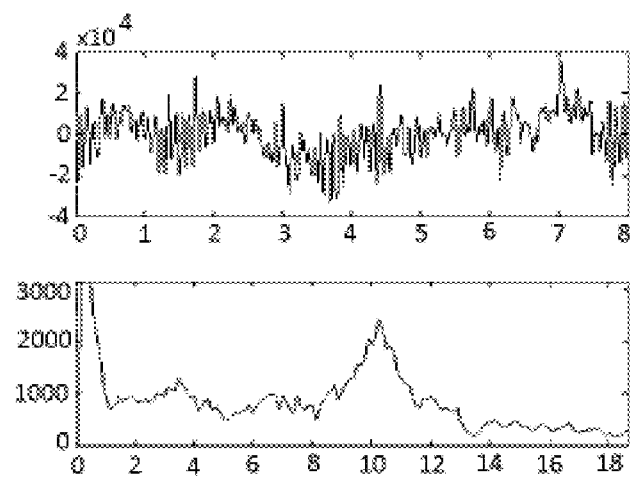
FIG. 5 is an illustrative example of raw EEG waveforms (top panel of image per phase) and FFT waveforms for the raw EEG waveform (bottom panel of image per phase).
Figure 5:
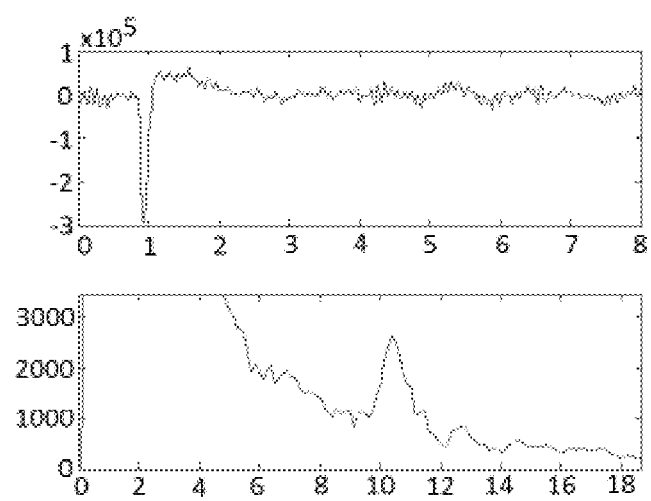
Figure 5:
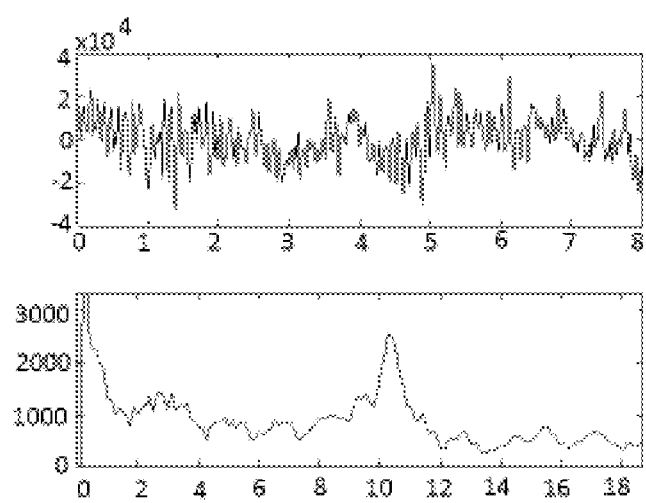

FIG. 5 shows non-limiting exemplary waveforms from EEGs recorded in one of the test subject the study is shown. One image is shown per phase. The images were selected as a "typical" 8-second epoch from the entire recording. The top waveform in each image of a phase is the raw EEG. The bottom waveform in each image of a phase is a 1028 point (128 Hz sample rate) FFT for the raw EEG waveform, showing the frequency of the dominant peak. Some of the subjects have two images shown for one phase, in order to exemplify variations in alpha activity throughout the recording (not shown).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of determining a final intrinsic alpha frequency (fIAF) of a subject in a neuro-electroencephalogram (EEG) synchronization therapy comprising:
   applying an EEG discrimination routine executed by one or more processors and comprising:
   a) receiving a first EEG recording obtained from an EEG sensor in a time domain;
   b) segmenting the first EEG recording into a plurality of epochs, each of the plurality of epochs comprising a segment of data, wherein a total number of epochs is N;
   c) filtering the segment of data of each epoch using a high-pass filter;
   d) converting each epoch into a frequency domain epoch (i);
   e) filtering each frequency domain epoch (i) using a smoothing filter;
   f) calculating an epoch intrinsic alpha frequency ($m_i$) of each frequency domain epoch (i);
   g) calculating a mean (M) intrinsic alpha frequency (IAF) of all intrinsic alpha frequencies ($m_{i-N}$), wherein $$M = \frac{1}{N}\sum_{i=1}^{N} m_i;$$

h) determining a farthest frequency domain epoch ($m_f$) from the M,
       if $|m_f - M| > 0.5$ hertz(Hz), removing the farthest frequency domain epoch ($m_f$), decrementing N, and returning to step g), or
       if $|m_f - M| \leq 0.5$ Hz, continuing to next step;
   i) setting fIAF equal to M; and
   j) outputting the fIAF to a therapy device that delivers a low amplitude stimulation; and
   delivering, with the therapy device, low amplitude stimulation at the fIAF.

2. The method of claim 1, wherein a length of the first EEG recording is 128 seconds.

3. The method of claim 1, wherein the first EEG recording comprises a single-channel recording.

4. The method of claim 1, wherein the first EEG recording comprises a multi-channel recording, wherein an IAF estimate is made for each channel in an epoch and averaged together, or wherein each channel is treated separately, generating an IAF estimate for each channel for the full EEG recording, and wherein valid IAF estimates from each channel, as determined by step h), are averaged together to generate an fIAF.

5. The method of claim 4, wherein a channel intrinsic alpha frequency is determined for each channel in the frequency domain epoch (i), and are averaged to generate the epoch intrinsic alpha frequency ($m_i$).

6. The method of claim 1, wherein a channel of the first EEG recording initially comprises 16 epochs.

7. The method of claim 1, wherein the epoch intrinsic alpha frequency ($m_i$,) of each frequency domain epoch (i) is calculated from 7.0 Hz to 14.0 Hz.

8. The method of claim 1, wherein the fIAF is from 8.0 Hz to 13.0 Hz.

9. The method of claim 1, wherein the first EEG recording comprises a sample rate of 128 samples/sec.

10. The method of claim 1, wherein the epoch intrinsic alpha frequency of each epoch ($m_i$) is determined using a Fast Fourier Transform (FFT).

11. The method of claim 1, wherein if a standard deviation (SD) of the N epoch IAF values ≥0.75 Hz, a second EEG recording is obtained and the method of claim 1 is repeated using the second EEG recording in place of the first EEG recording.

12. The method of claim 11, wherein if a second standard deviation (SD) of the N epoch IAF values ≥0.75 Hz, a third EEG recording is obtained and the method of claim 1 is repeated using the third EEG recording in place of the first EEG recording.

13. The method of claim 12, wherein if a third standard deviation (SD) of the N epoch IAF values ≥0.75 Hz, a range of fIAFs of the first EEG recording, the second EEG recording, and the third EEG recording is calculated, wherein if the range is <2.0 Hz, then the mean value of the fIAFs of the first EEG recording, the second EEG recording, and the third EEG recording is determined to be a valid intrinsic alpha frequency (vIAF).

14. The method of claim 1, wherein if the fIAF is <8.0 Hz or >13.0 Hz, a second EEG recording is obtained and the method of claim 1 is repeated using the second EEG recording in place of the first EEG recording.

15. The method of claim 14, wherein if the fIAF calculated using the second EEG recording is <8.0 Hz or >13.0 Hz, a third EEG recording is obtained and the method of claim 1 is repeated using the third EEG recording in place of the first EEG recording.

16. The method of claim 15, wherein if the fIAF calculated using the third EEG recording is <8.0 Hz or >13.0 Hz, a range of fIAFs of the first EEG recording, the second EEG recording, and the third EEG recording is calculated, wherein if the range is <2.0 Hz, then the mean value of the fIAFs of the first EEG recording, the second EEG recording, and the third EEG recording is determined to be a valid intrinsic alpha frequency (vIAF).

17. The method of claim 1, wherein if the fIAF of the EEG is from 8.0 Hz to 13.0 Hz and a standard deviation (SD) of the N epoch IAF values is <0.75 Hz, the fIAF is determined to be a valid intrinsic alpha frequency (vIAF).

18. The method of claim 1, wherein
if a standard deviation (SD) of the N epoch IAF values ≥0.75 Hz, or
if the final intrinsic alpha frequency (fIAF) is <8.0 Hz or >13.0 Hz, then a second EEG recording is obtained and the method of claim 1 is repeated using the second EEG recording in place of the first EEG recording.

19. The method of claim 18, wherein
if a standard deviation (SD) of the N epoch IAF values calculated using the second EEG reading ≥0.75 Hz, or
if the final intrinsic alpha frequency (fIAF) calculated using the second EEG reading is <8.0 Hz or >13.0 Hz, then a third EEG recording is obtained and the method of claim 1 is repeated using the third EEG recording in place of the first EEG recording.

20. The method of claim 19, wherein if the fIAF calculated using the third EEG recording is <8.0 Hz or >13.0 Hz or if the standard deviation (SD) of the N epoch IAF values calculated using the third EEG reading ≥0.75 Hz, a range of fIAFs of the first EEG recording, the second EEG recording, and the third EEG recording is calculated, wherein if the range is <2.0 Hz, then the mean value of the fIAFs the first EEG recording, the second EEG recording, and the third EEG recording is determined to be a valid intrinsic alpha frequency (vIAF).

* * * * *